(12) United States Patent
Longley

(10) Patent No.: US 10,679,483 B2
(45) Date of Patent: Jun. 9, 2020

(54) GAS MONITORING AND ALARM SYSTEMS AND METHODS

(71) Applicant: ELEVEN ELEVEN TECHNOLOGIES, LLC, Las Vegas, NV (US)

(72) Inventor: Ronald V. Longley, Las Vegas, NV (US)

(73) Assignee: ELEVEN ELEVEN TECHNOLOGIES, LLC, Las Vegas, NV (US)

( * ) Notice: Subject to any disclaimer, the term of this patent is extended or adjusted under 35 U.S.C. 154(b) by 0 days.

(21) Appl. No.: 16/112,536

(22) Filed: Aug. 24, 2018

(65) Prior Publication Data

US 2019/0139392 A1    May 9, 2019

Related U.S. Application Data

(60) Provisional application No. 62/633,451, filed on Feb. 21, 2018, provisional application No. 62/550,497, filed on Aug. 25, 2017.

(51) Int. Cl.
*G08B 21/14* (2006.01)
*G01N 33/00* (2006.01)

(52) U.S. Cl.
CPC ........... *G08B 21/14* (2013.01); *G01N 33/004* (2013.01); *G01N 33/0063* (2013.01)

(58) Field of Classification Search
None
See application file for complete search history.

(56) References Cited

U.S. PATENT DOCUMENTS

| 6,344,798 B1 * | 2/2002 | Schell | G08B 17/117 200/61.03 |
| 6,628,396 B1 * | 9/2003 | Gul | G01N 21/1702 250/343 |
| 8,314,712 B2 * | 11/2012 | Fromme | G01N 27/00 340/632 |
| 10,089,849 B2 * | 10/2018 | Liu | H04Q 9/00 |
| 10,156,552 B2 * | 12/2018 | Maddila | G01N 33/0006 |

(Continued)

OTHER PUBLICATIONS https://www.co2meter.com/collections/products, 2 pages, downloaded Nov. 21, 2018.

(Continued)

*Primary Examiner* — Chico A Foxx
(74) *Attorney, Agent, or Firm* — Howard & Howard Attorneys PLLC

(57) ABSTRACT

A gas monitoring and alarm system comprises a master monitor and at least one remote monitor. The master monitor is coupled to a master sensor that senses a concentration of a gas in a first area and sends data to the master monitor. The at least one remote monitor is communicatively coupled to the master monitor. The least one remote monitor is coupled to a remote sensor, which senses a concentration of gas in a second area. The at least one remote monitor receives data about the concentration of the gas in the second area from the remote sensor, and sends the data to the master monitor. The master monitor receives the data and triggers a first alarm status when the concentration of gas in at least one of the first area and the second area exceeds a first predefined alarm threshold.

15 Claims, 30 Drawing Sheets

(56) References Cited

U.S. PATENT DOCUMENTS

| | | | | |
|---|---|---|---|---|
| 10,377,206 B2* | 8/2019 | Kehoe | ............... | B60H 1/008 |
| 2002/0070869 A1* | 6/2002 | Dungan | ............ | G01N 33/0073 |
| | | | | 340/632 |
| 2004/0056771 A1* | 3/2004 | Dungan | ............ | G01N 33/0075 |
| | | | | 340/632 |
| 2007/0193132 A1* | 8/2007 | Roscioli | ............... | B32B 7/12 |
| | | | | 52/169.6 |
| 2017/0348047 A1* | 12/2017 | Reiter | ............ | A61B 18/1487 |
| 2018/0206099 A1* | 7/2018 | O'Connor | ............ | G01K 1/026 |

OTHER PUBLICATIONS https://www.analoxsensortechnology.com/hospitality/, 4 pages, downloaded Nov. 21, 2018.
https://www.logico2.com/products/, 13 pages, downloaded Nov. 21, 2018.

\* cited by examiner

GAS MONITORING AND ALARM SYSTEMS AND METHODS

CROSS-REFERENCE TO RELATED APPLICATIONS

This application claims benefit of U.S. Provisional Patent Application Ser. No. 62/550,497, filed on Aug. 25, 2017, and U.S. Provisional Patent Application Ser. No. 62/633,451, filed on Feb. 21, 2018, the entire contents of which are herein incorporated by reference.

TECHNICAL FIELD

The present invention generally concerns systems and methods for gas monitors and alarms. More specifically, the invention discloses systems and methods for monitoring gas levels and triggering alarms when high gas levels are detected.

BACKGROUND OF THE INVENTION

Many residential homes and business facilities utilize appliances and other systems that contain or emit gas that is harmful to humans at or above certain concentrations. For instance, many businesses that offer food and drink utilize soda-dispensing machines that use carbon dioxide to carbonate beverages. Carbon dioxide is lethal to humans above a certain concentration, but it is typically kept in cylinders that are intended to keep the gas contained and within safe concentrations for humans working in close contact with the gas. In the event of a leak, however, the concentration of the gas can rise rapidly to unsafe levels, especially in small, confined areas. Carbon dioxide, like many gases, is odorless and colorless, and thus cannot be detected by humans even in hazardously high concentrations without the aid of a gas monitoring system.

Existing gas monitoring and/or alarm systems merely sense the presence of a gas and may alert those nearby to its presence. Some systems may also alert emergency responders, such as the fire department. However, these systems are not designed to also trigger evacuation of the gas to quickly bring the concentration of the gas in the area back down to a safe level. Moreover, many of these systems are not designed with mechanisms for providing power backup to these lifesaving systems that may otherwise cease operating in the event of a power failure.

Additionally, existing gas monitors typically have an integrated sensor such that the sensor unit and the monitor itself must be physically located in the same area. This is problematic if a user must be near the monitor to know whether gas levels in an area are unsafe; by the time the user is close enough to see the monitor, the user may have already entered a potentially hazardous area. Additionally, most current systems utilize a standalone monitor requiring its own power source. If multiple areas within a building (e.g., different rooms in a building) are being monitored, an entirely separate sensor must be installed in each area.

Gas monitoring and alarm systems designed to overcome one or more of the aforementioned challenges are desired.

BRIEF DESCRIPTION OF THE DRAWINGS

Other advantages of the present invention will be readily appreciated as the same becomes better understood by reference to the following detailed description when considered in connection with the accompanying drawings wherein.

SUMMARY OF THE INVENTION

Figure 1:
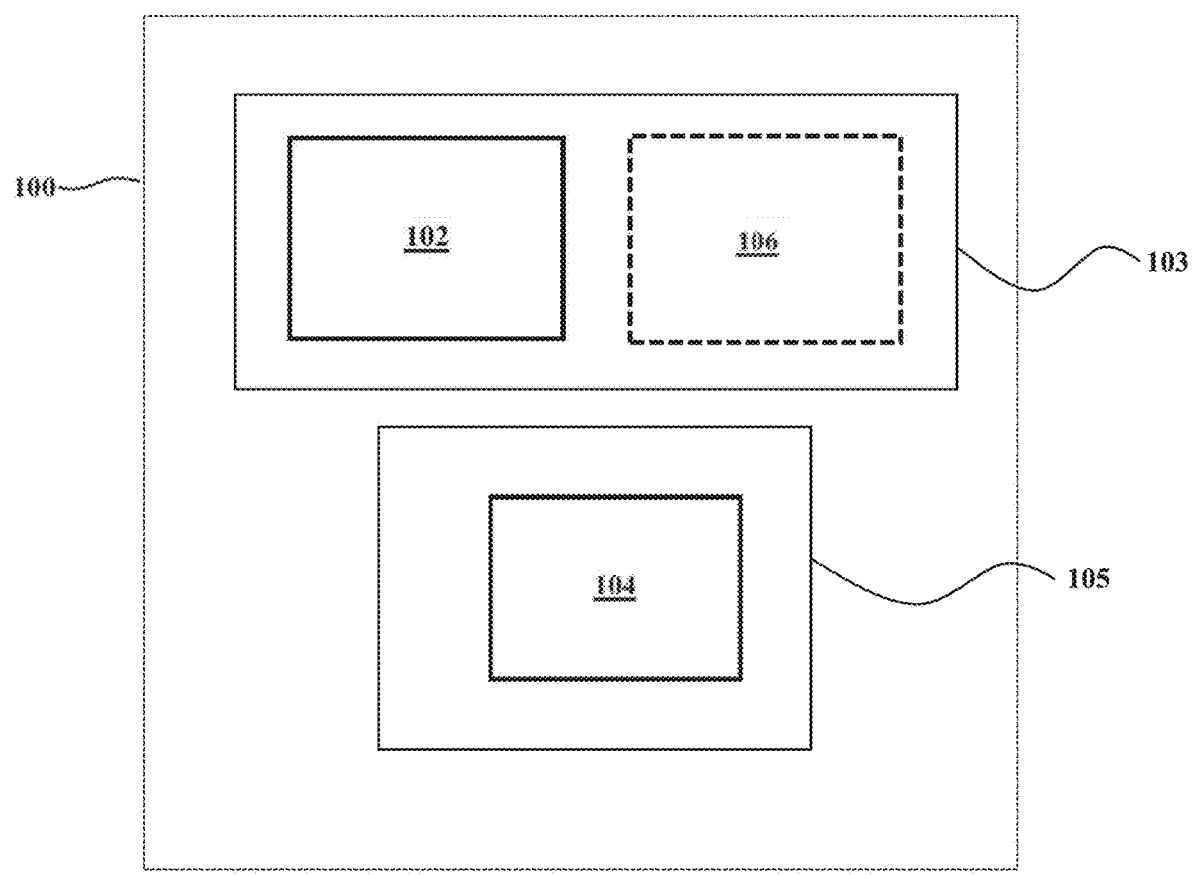
FIG. 1 is a block diagram of a gas monitoring and alarm system.

In one aspect of the present invention, a system is disclosed. The system includes a master monitor and at least one remote monitor. The master monitor is coupled to a master sensor that senses a concentration of a gas in a first area and sends data to the master monitor. The at least one remote monitor is communicatively coupled to the master monitor. The least one remote monitor is coupled to a remote sensor, which senses a concentration of gas in a second area. The at least one remote monitor receives data about the concentration of the gas in the second area from the remote sensor, and sends the data to the master monitor. The master monitor receives the data and triggers a first alarm status when the concentration of gas in at least one of the first area and the second area exceeds a first predefined alarm threshold.

In yet another aspect of the present invention, a system is disclosed. The system includes a master monitor and at least one remote monitor. The master monitor is coupled to a master sensor, which is configured to sense a concentration of a gas in a first area and send data about the concentration of the gas to the master monitor. The at least one remote monitor is communicatively coupled to the master monitor. The at least one remote monitor is configured to receive data about the concentration of the gas from the master monitor. The master monitor is further configured to trigger a first alarm status when the concentration of gas in the first area exceeds a first predefined alarm threshold, send data about the alarm status to the remote monitor, and activate an alarm system when the alarm status is triggered.

In another aspect of the present invention, a method is disclosed. A master monitor coupled to a master sensor is provided. The master sensor configured to sense a concentration of a gas in a first area and send data about the concentration of the gas to the master monitor. At least one remote monitor communicatively coupled to the master monitor is provided. The at least one remote monitor is coupled to a remote sensor configured to sense a concentration of gas in a second area. The at least one remote monitor receives data about the concentration of the gas in the second area from the remote sensor. The at least one remote monitor sends the data to the master monitor. The master monitor receives the data from the at least one remote monitor. The master monitor triggers a first alarm status when the concentration of gas in at least one of the first area and the second area exceeds a first predefined alarm threshold.

DETAILED DESCRIPTION OF THE INVENTION

Embodiments of the present invention provide systems and methods for monitoring and detection of gas levels, and triggering alarms when high levels of gas(es) are detected. Persons of ordinary skill in the art will realize that the following description of the presently invention is illustrative only and not in any way limiting. Other embodiments of the invention will readily suggest themselves to such skilled persons. According to the present invention, a system may include any combination of a gas monitoring and/or detection system and/or an alarm system.

Gas Monitoring and Alarm System with Optional Relay Interface

Referring to FIG. 1, a block diagram of a gas monitoring and alarm system is shown. A gas monitoring and alarm system 100 comprises a primary monitor 102, a remote display unit 104, and an optional relay interface 106. Primary monitor 102 and relay interface 106 may be located at a source location 103. Remote display unit 104 may be located at a remote location 105. In some embodiments, there may be more than one remote location 105 if there are more than one remote display units 104 being utilized by system 100. In some embodiments, the relay interface 106 may be an optional component of system 100.

Figure 2:
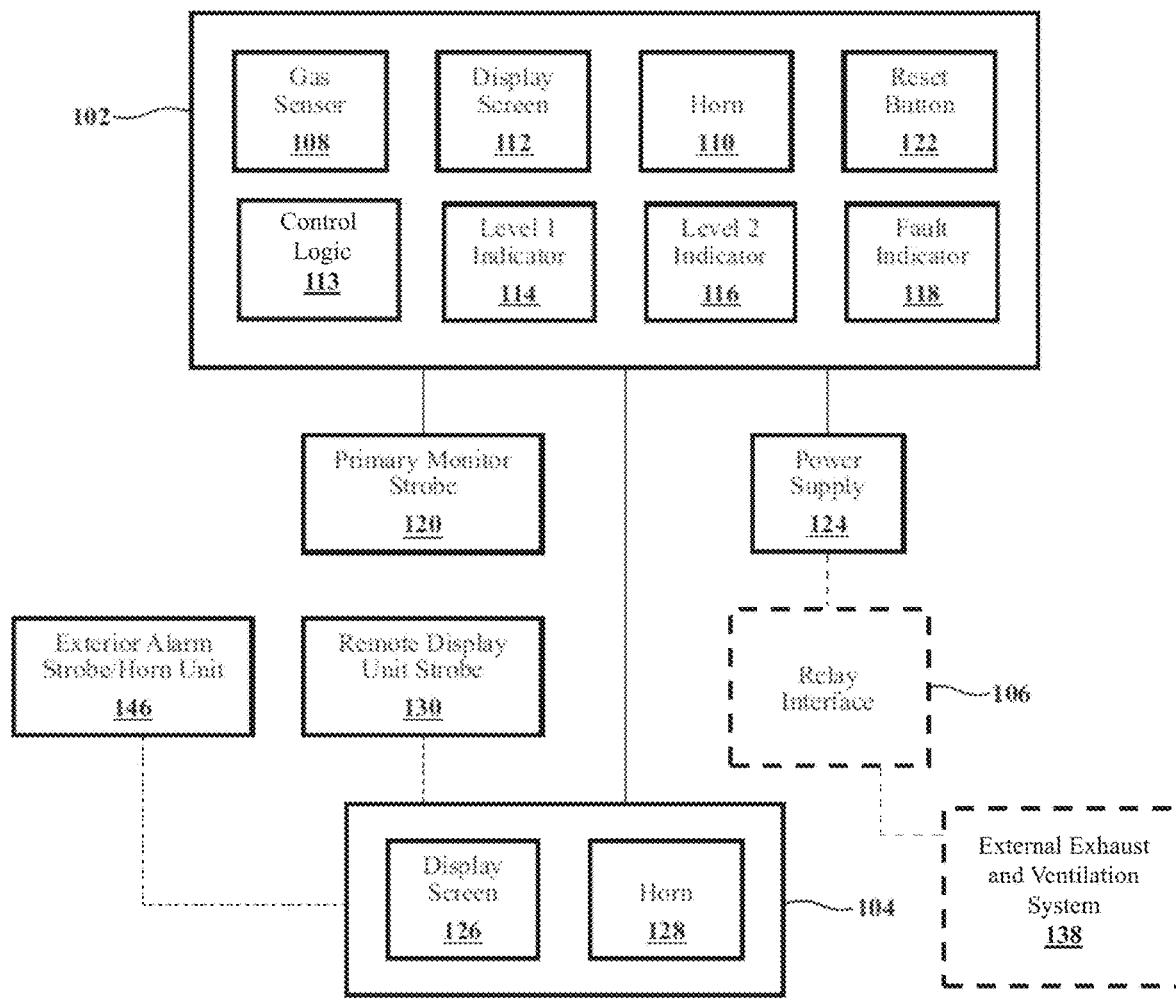
FIG. 2 is a block diagram of a primary monitor, a remote display unit, and a relay interface of the gas monitoring and alarm system of FIG. 1.

Referring now to FIG. 2, a block diagram of a primary monitor, a remote display unit, and an optional relay interface of the gas monitoring and alarm system of FIG. 1 is shown. Primary monitor 102 comprises a gas sensor 108, a primary monitor horn 110, a primary monitor display screen 112, and a control logic 113. Control logic 113 may be a computer, including a microprocessor, a programmable logic controller, or any other type of suitable controller for receiving sensor information and performing the operations described herein, including controlling horn/strobes, display screen of the primary monitor 102 and indicators thereof, the display of remote display unit 104 and indicators thereof, and relay interface 106, as described in more detail below. Primary monitor 102 further comprises a first alarm level indicator 114, a second alarm level indicator 116, a fault indicator 118, reset button 122, and internal relays 127, 129. In some embodiments, primary monitor 102 and/or remote display unit 104 may be configured to connect to, and send and receive data over, a wireless network, such as a WiFi network, cellular, or other network which enables primary monitor 102 and/or remote display unit 104 to send, for example, status reports and other data to remote locations and devices outside of system 100.

The first alarm level may be adjustable to a first predefined concentration threshold. For instance, in the embodiment shown, a factory default setting is a concentration of $CO_2$ at 1.5% or 15,000 parts per million (PPM). The second alarm level may also be adjustable to a second predefined concentration threshold. For instance, in the embodiment shown, a factory default setting is a concentration of $CO_2$ at 3% or 30,000 parts per million (PPM). Thus, the two-level alarm system may allow detection of a gas at varying concentrations, with varying responses to gas detection at each level. Primary monitor display screen 112 may display information about the detected concentration levels of a gas.

Primary monitor 102 is activated when a gas is detected by the gas sensor 108. In the embodiments shown herein, gas sensor 108 detects carbon dioxide ($CO_2$), but it will be understood that the present invention may be used to detect any gas at any concentration. When gas sensor 108 senses a gas at a concentration at or above the first predefined concentration threshold, the first alarm level indicator 114 and primary monitor horn 110 may be activated. First alarm level indicator 114 may comprise, for example, a blinking light, such as a red LED light. Primary monitor horn 110 may emit intermittent sounds at a predefined decibel level. Moreover, primary monitor 102 is connected to primary monitor strobe 120, which may be external to primary monitor 102. Primary monitor strobe 120 may begin to flash when the first alarm level is activated.

If gas sensor 108 detects that the concentration of the gas drops below the first predefined concentration threshold, first alarm level indicator 114 may discontinue blinking, primary monitor horn 110 may discontinue sounding, and primary monitor strobe 120 may discontinue flashing.

If gas sensor 108 detects that the concentration of the gas continues to rise above the second predefined concentration threshold, first alarm level indicator 114 will continue to blink. Primary monitor horn 110 may continue sounding and primary monitor strobe 120 may continue flashing, both at an increased tempo. Additionally, second alarm level indicator 116 may be activated. Second alarm level indicator 116 may comprise a blinking light, such as a red LED light.

Moreover, when the concentration of the gas meets or exceeds the second predefined concentration threshold, fault indicator 118 may be activated. Fault indicator 118 may comprise a flashing light, such as an amber LED light. Fault indicator 118 may continuously flash until primary monitor 102 is reset, either by pressing a reset button 122 or disrupting a power supply 124 connected to primary monitor 102.

If gas sensor 108 detects that the concentration of the gas drops below the second predefined concentration and the first predefined concentration threshold, first alarm level indicator 114 and second alarm level indicator 116 may discontinue blinking, primary monitor horn 110 may discontinue sounding, and primary monitor strobe 120 may discontinue flashing. If gas sensor 108 detects that the concentration of the gas drops below the second predefined concentration but is still above the first predefined concentration threshold, second alarm level indicator 116 may discontinue blinking, but first alarm level indicator 114 may continue blinking and primary monitor horn 110 may continue sounding, and primary monitor strobe 120 may continue flashing, until gas sensor 108 detects that the concentration of the gas has dropped below the first predefined concentration threshold.

Primary monitor 102 is further coupled to remote display unit 108 (e.g., by a CAT6 cable, a CAT5 cable, or other Ethernet/network cable suitable to allow the primary monitor 102 to communicate with the remote display unit 108), which is intended to be placed externally to the primary monitor 102 and ideally in area separate from the gas-containing device that is being monitored (e.g., a $CO_2$ tank). Remote display unit 104 acts as an entry pre-warning device, such that it can be conveniently observed by a person before they enter the room where the primary monitor 102 and the gas-containing device are located. Remote display unit 104 may be a satellite information repeater, and displays the measurements made by primary monitor 102 on a remote display unit screen 126, such as a digital LCD screen. In some embodiments, there may be more than one remote display unit 104, which may be in more than one remote location. Remote display unit 104 further comprises a remote display unit horn 128, and is coupled to a remote display unit strobe 130. When the first alarm level and the second alarm level of primary monitor 104 are activated, remote display unit horn 128 and remote display unit horn strobe 130 are activated. When gas concentrations drop below the first predefined concentration threshold, remote display unit horn 128 and remote display unit horn strobe 130 will disengage. In some embodiments, remote display unit 104 may instead be controlled by a distinct controller separate from the control logic 113, such that the remote display unit controller controls the operations related to the remote display unit 104 (e.g., operation of the remote display unit horn 128, remote display unit screen 126, etc.). In some embodiments, the controllers of the primary monitor 102 and the remote display unit 104 may be in communication over a network, such as a wireless, cellular, Ethernet, or LAN network, or any other suitable network to facilitate communication between the controllers.

In some embodiments, primary monitor 102 and/or remote display unit 104 may be capable of communicating over a wireless network such as a WiFi network, cellular, or other network which enables primary monitor 102 and/or remote display unit 104 to send and receive, for example, status reports and other data to and from remote locations and devices outside of system 100.

Activation of the first alarm level of primary monitor 102 may, in some embodiments, trigger an internal relay system that activates a relay interface 106. Relay interface 106 is discussed in more detail with respect to the various embodiments disclosed below.

Relay Interface First Embodiment

Figure 3:
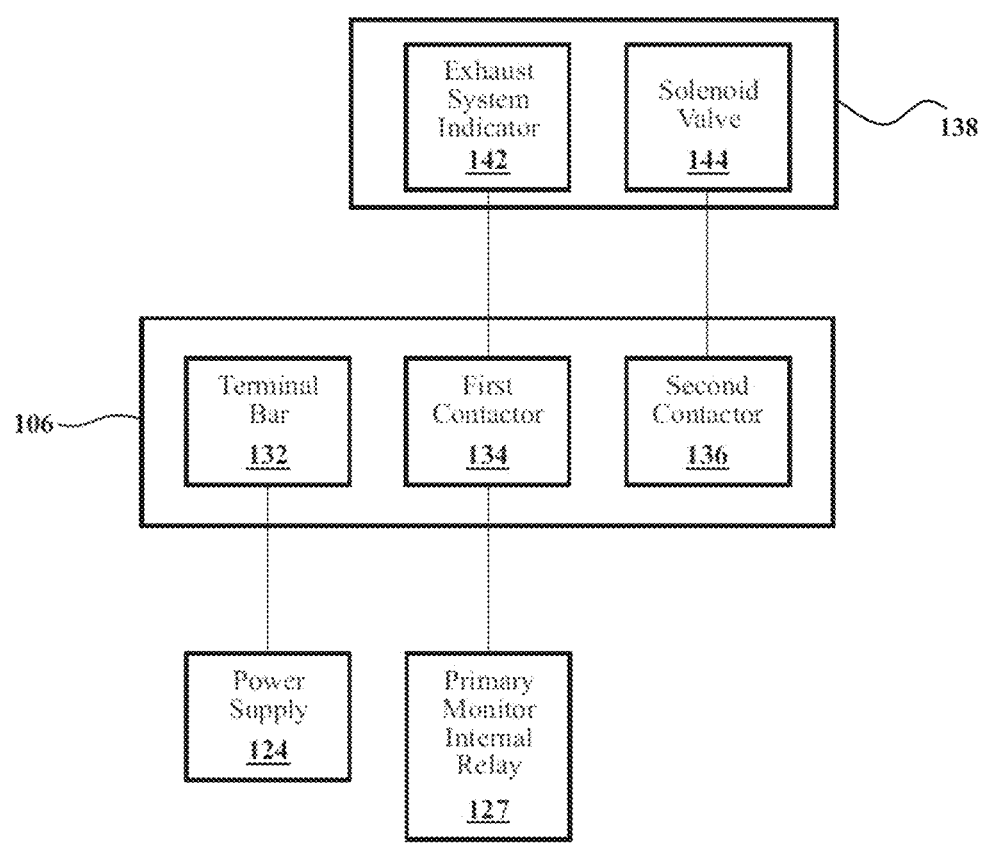
FIG. 3 is a block diagram of a relay interface of a gas monitoring and alarm system according to a first embodiment.

Referring now to FIG. 3, a block diagram of a relay interface of a gas monitoring and alarm system according to a first embodiment is shown. Relay interface 106 comprises a terminal bar 132, a first contactor 134, and a second contactor 136. Terminal bar 132 generates a power supply, fed from power supply 124, to deliver to first contactor 134. First contactor 134 may be a 120-volt multi-purpose contactor, rated at 40 amps at 240 volts. First contactor 134 creates a circuit that is normally open and is energized by one of the primary monitor 102 internal relays 127, 129 upon its activation during alarm status. When first contactor 134 is energized, it closes the circuit that supplies power to an external exhaust ventilation system 138, thereby allowing evacuation of gas when gas concentrations are at or above unsafe levels.

First contactor 134 is also coupled to second contactor 136. Second contactor 136 may be a 120-volt contactor, rated at 15 amps at 240 volts. Second contactor 136 creates a circuit that is normally closed. The closed circuit is deactivated by the first contactor 134 when it is energized by one of the primary monitor 102 internal relays upon its activation during alarm status. Second contactor 136 is used to control power to a solenoid valve 140. During normal operation, gas is allowed to flow freely though solenoid valve 140 that is powered by a 120-volt circuit that is normally closed. However, when high concentrations of gas are detected and primary monitor 102 internal relays are activated, power is supplied to first contactor 134, thereby closing its circuit that is normally open. When this happens, power is supplied to exhaust ventilation system 138. Furthermore, when first contactor 134 is energized, it disrupts power to the second contactor's circuit that is normally closed, there by breaking the circuit, closing solenoid valve 140, and disrupting gas flow.

Figure 4A:
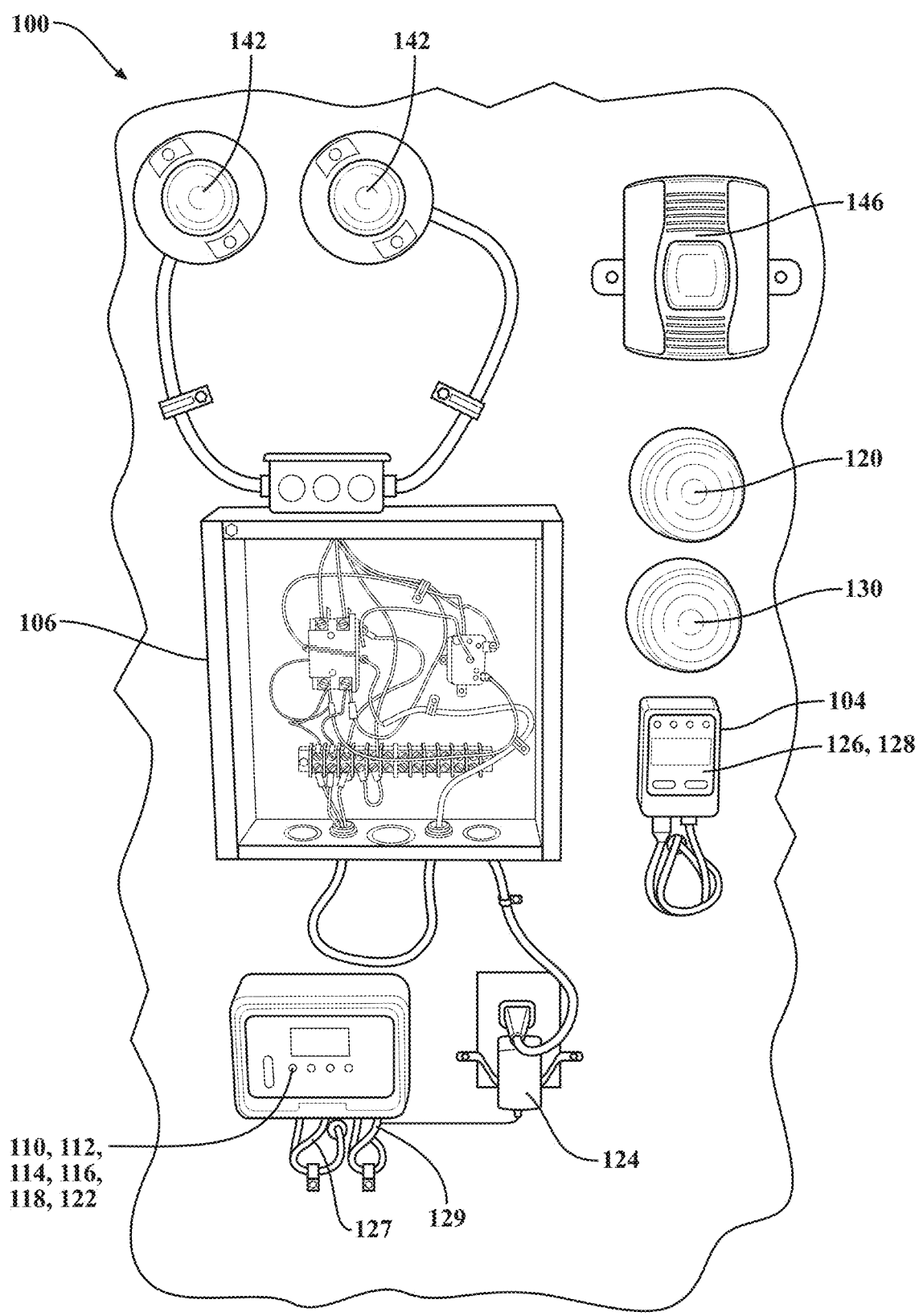
FIG. 4A is a front view of an exemplary gas monitoring and alarm system according to the first embodiment.
Figure 4B:
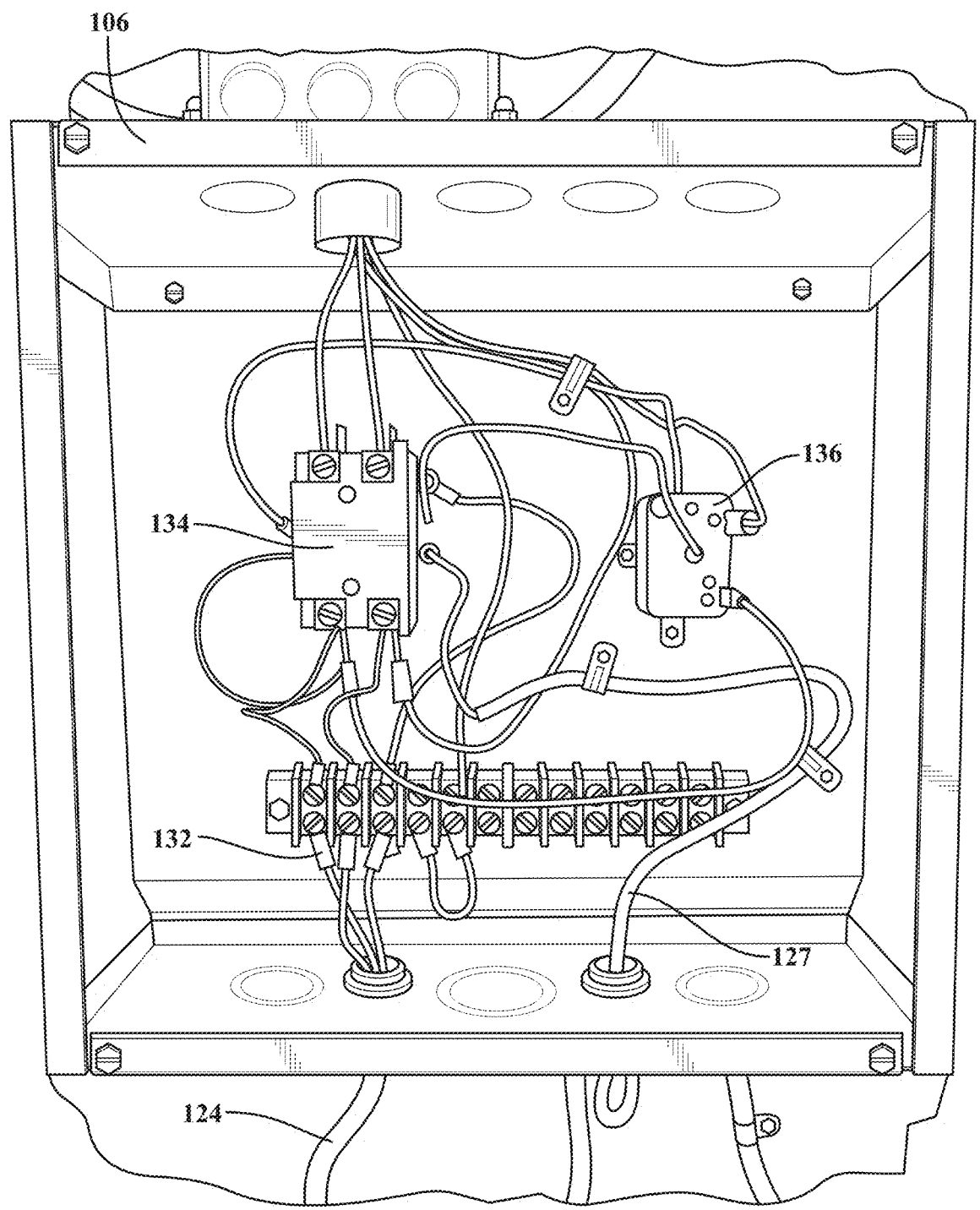
FIG. 4B is a front view of a relay interface of the gas monitoring and alarm system of FIG. 4A.

Referring now to FIGS. 4A-4B, front views of an exemplary gas monitoring and alarm system and its relay interface according to the first embodiment are illustrated. FIG. 4A further shows external exhaust ventilation indicator 142 and solenoid valve indicator 144 that are included for illustration/demonstration purposes only. External exhaust ventilation system indicator 142 represents the exhaust ventilation system 138, normally an open circuit. Solenoid valve indicator 144 represents the solenoid valve 140, normally a closed circuit. FIG. 4A further includes optional additional exterior strobe/horn unit 146 that may be used in conjunction with the existing horns/strobes of the system as an additional safety mechanism.

Relay Interface Second Embodiment

Figure 5:
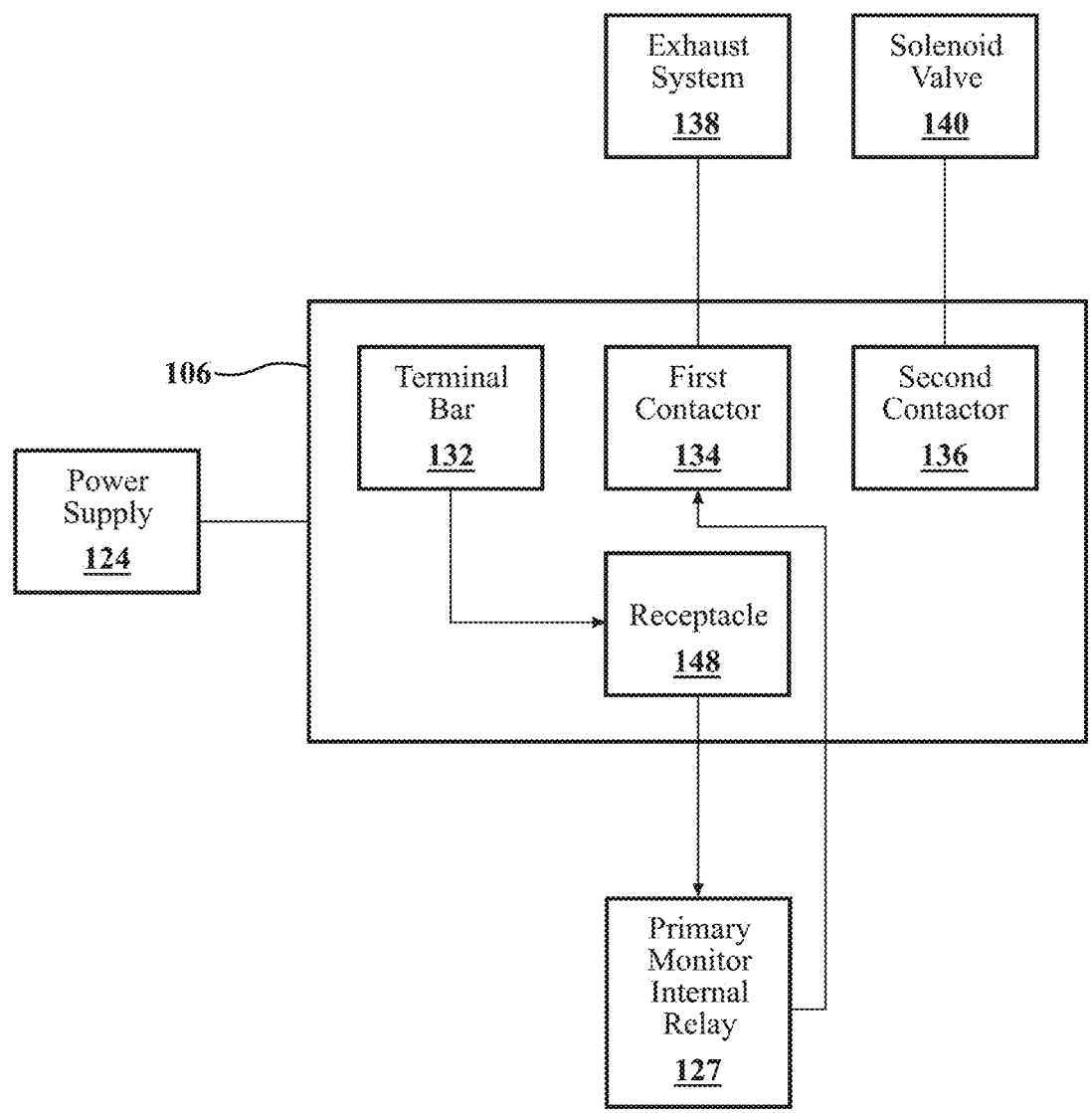
FIG. 5 is a block diagram of a relay interface of the gas monitoring and alarm system according to a second embodiment.

Referring now to FIG. 5, a block diagram of a relay interface of the gas monitoring and alarm system according to a second embodiment is shown. Relay interface 106 comprises a terminal bar 132, a first contactor 134, a second contactor 136, and a receptacle 148. Terminal bar 132 generates a power supply, fed from power supply 124, to deliver to first contactor 134. Terminal bar 132 and first contactor 134 together supply power to exhaust ventilation system 138 and solenoid valve 140. Terminal bar 132 also delivers power to receptacle 148. Receptacle 148 may be a 120-volt receptacle that, in turn, supplies power to primary monitor 102.

First contactor 134 may be a 120-volt definite-purpose contactor (3 Pole), rated at 40 amps at 240 volts. First contactor 134 creates a circuit that normally open and is energized by one of the primary monitor 102 internal relays upon its activation during alarm status. When first contactor 134 is energized, it closes the circuit that supplies power to the external exhaust ventilation system 138, thereby allowing evacuation of gas when gas concentrations are at or above unsafe levels.

First contactor 134 is also interfaced with second contactor 136. Second contactor 136 may be an auxiliary contactor, rated at 40 amps and carrying no voltage. Second contactor 136 creates a circuit that is normally closed. The closed circuit is deactivated by the first contactor 134 when it is energized by one of the primary monitor 102 internal relays upon its activation during alarm status. Second contactor 136 is used to control power to solenoid valve 140. During normal operation, gas is allowed to flow freely though solenoid valve 140 that is powered by a 120-volt circuit that is normally closed. However, when high concentrations of gas are detected and primary monitor 102 internal relays are activated, power is supplied to first contactor 134, thereby closing its circuit that is normally open. When this happens, power is supplied to exhaust ventilation system 138. Furthermore, when first contactor 134 is energized, it disrupts power to the circuit of second contactor 136 that is normally closed, there by breaking the circuit, closing solenoid valve 140, and disrupting gas flow.

Furthermore, according to this embodiment, relay interface 106 further comprises a receptacle 148, which provides power to primary monitor 102 instead of power supply 124 (see FIG. 2). Receptacle 148 may be a 120-volt receptacle, and is located inside relay interface 106 in order to make it more difficult for power to primary monitor 102 to be disrupted, since relay interface 106 may be encased in a closable (and, optionally, lockable) container to prevent or deter access to its components.

Figure 6A:
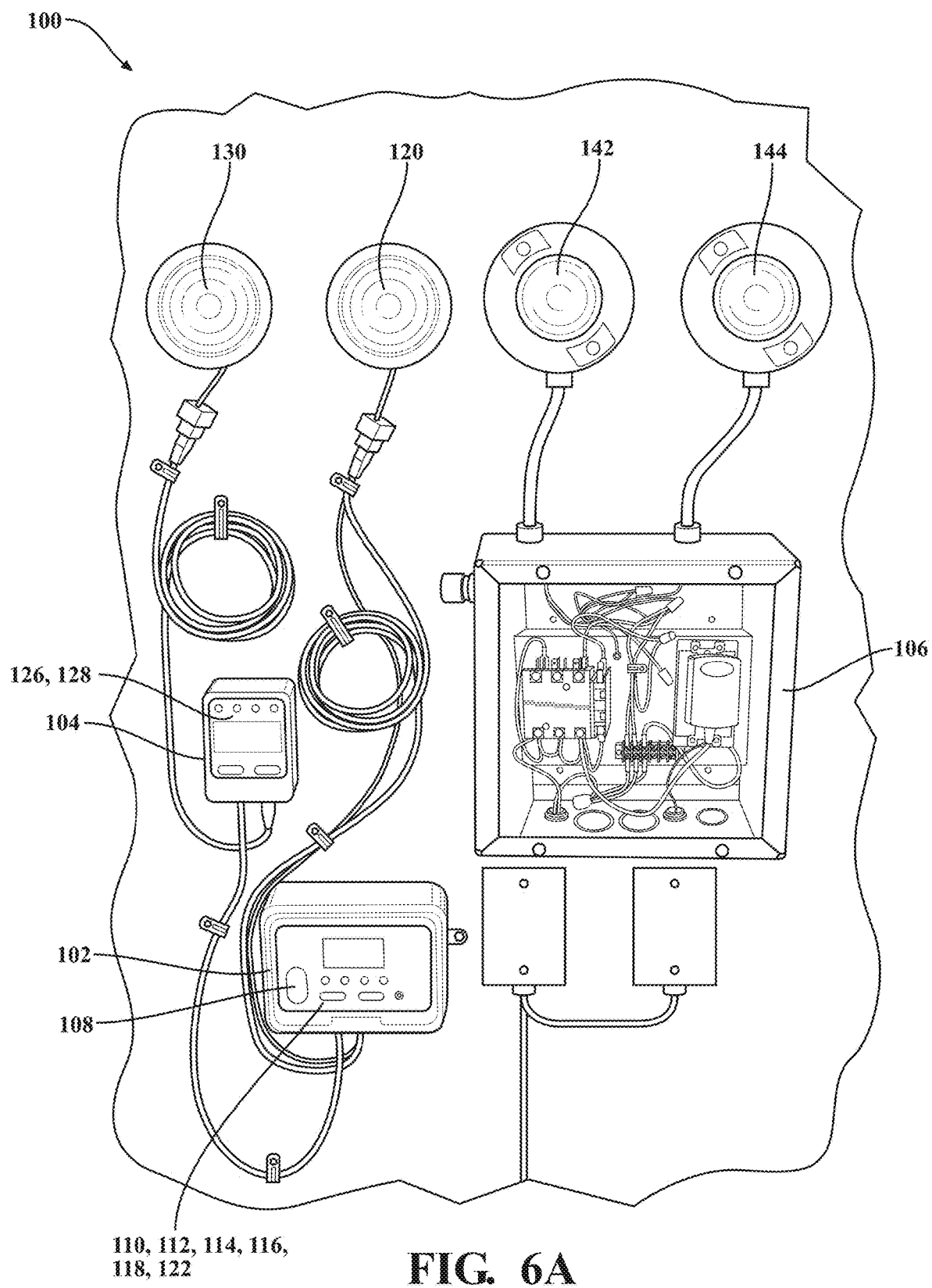
FIG. 6A is a front view of an exemplary gas monitoring and alarm system according to the second embodiment.
Figure 6B:
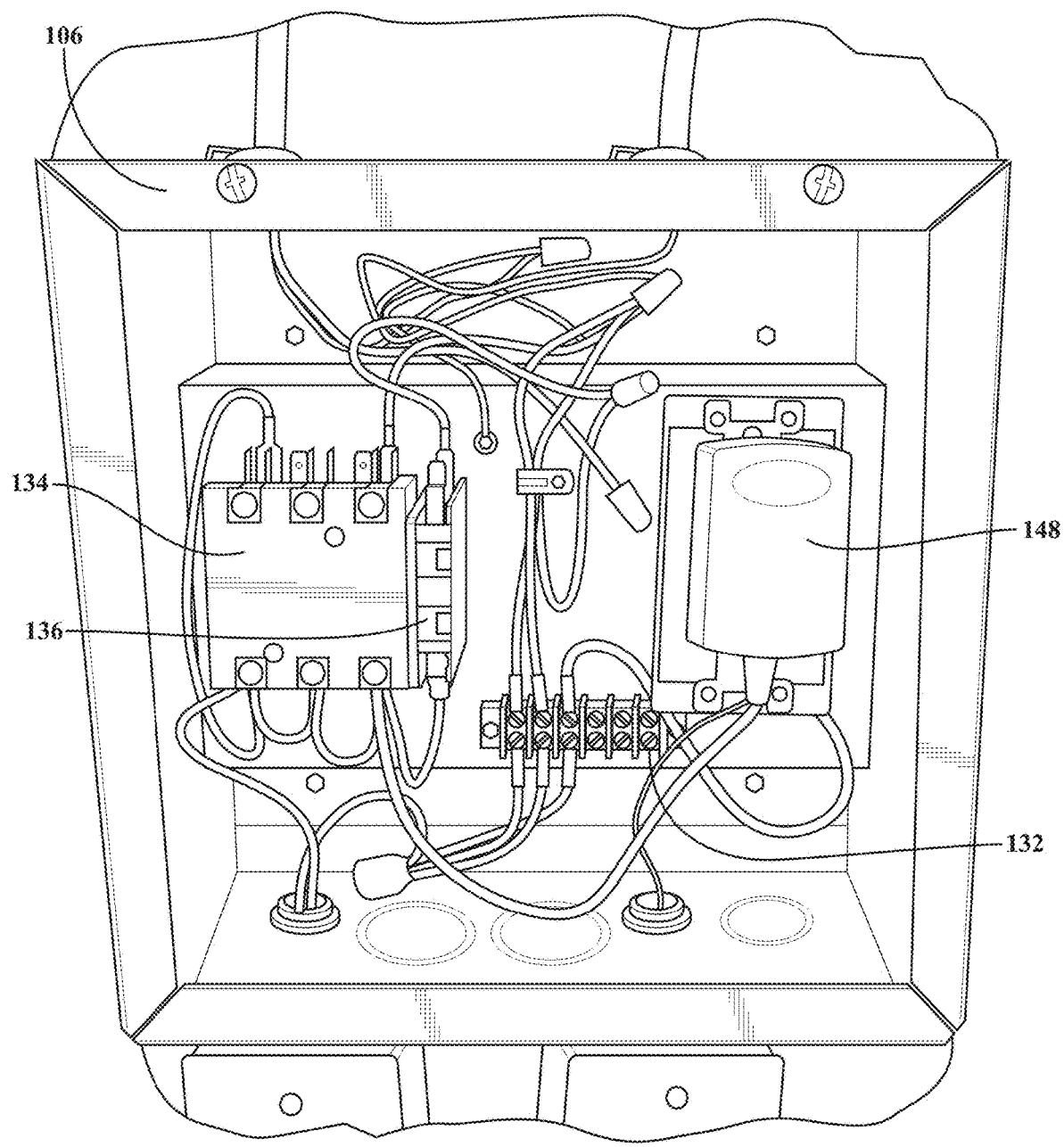
FIG. 6B is a front view of a relay interface of the gas monitoring and alarm system of FIG. 6A.

Referring now to FIGS. 6A-6B, front views of an exemplary gas monitoring and alarm system and its relay interface according to the second embodiment are illustrated. FIG. 6A further shows external exhaust ventilation system indicator 142 and solenoid valve indicator 144 that are included for illustration/demonstration purposes only. External exhaust ventilation system indicator 142 represents the exhaust ventilation system 138, normally an open circuit. Solenoid valve indicator 144 represents the solenoid valve 140, normally a closed circuit.

Relay Interface Third Embodiment

Figure 7:
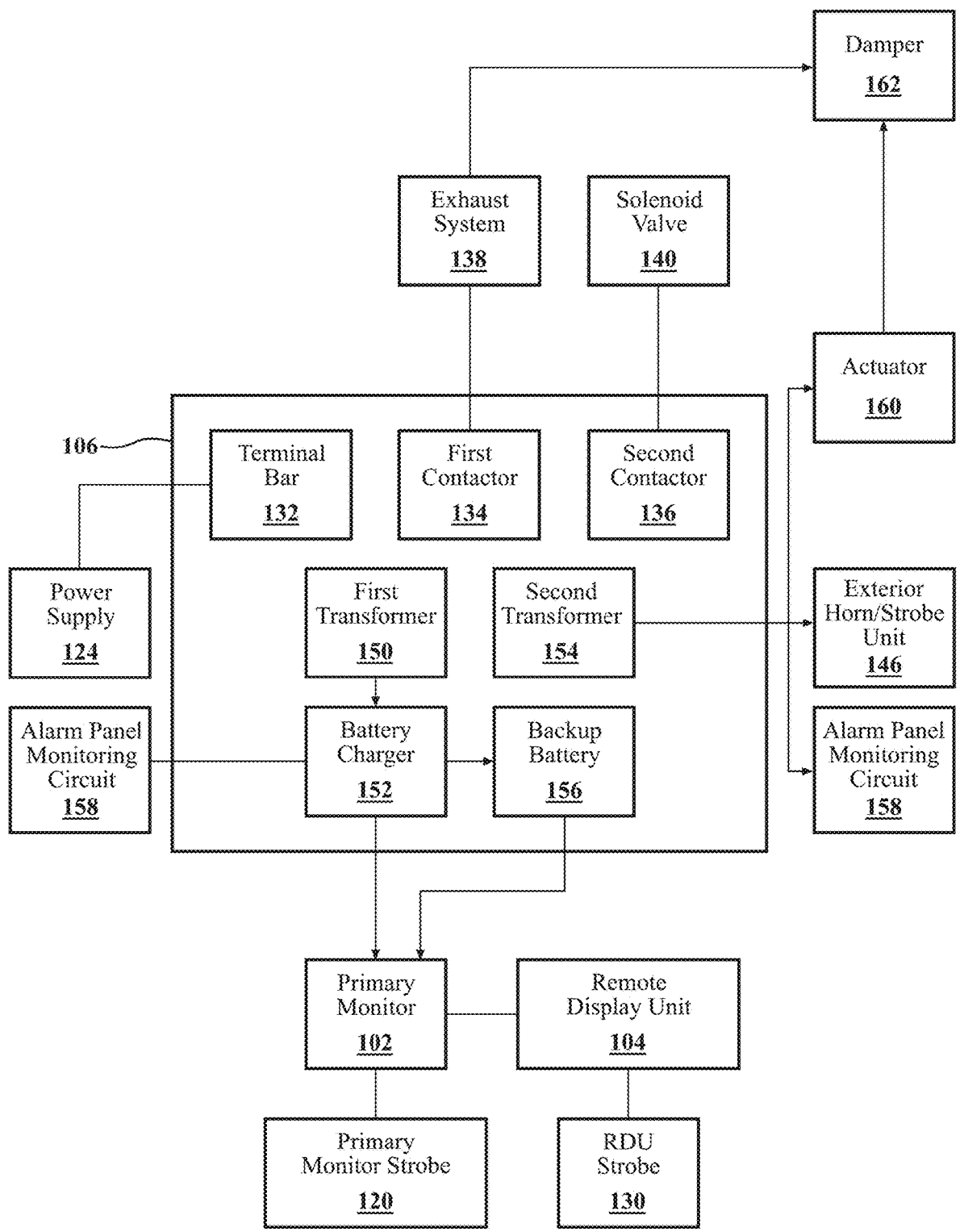
FIG. 7 is a block diagram of a relay interface of the gas monitoring and alarm system according to a third embodiment.

Referring now to FIG. 7, a block diagram of a relay interface of the gas monitoring and alarm system according to a third embodiment is shown. Relay interface 106 comprises terminal bar 132, first contactor 134, second contactor 136, a first transformer 150, a battery charger 152, a second transformer 154, and a backup battery 156.

Terminal bar 132 generates a power supply, fed from power supply 124, to deliver to first contactor 134. Terminal bar 132 and first contactor 134 together supply power to exhaust ventilation system 138 and solenoid valve 140. Terminal bar 132 also delivers power to first transformer 150 and second transformer 154.

First contactor 134 may be a 120-volt multi-purpose contactor (3 Pole), rated at 40 amps at 240 volts. First contactor 134 creates a circuit that normally open and is energized by one of the primary monitor 102 internal relays 127, 129 upon its activation during alarm status. When first contactor 134 is energized, it closes the circuit that supplies power to an external exhaust ventilation system 138, thereby allowing evacuation of gas when gas concentrations are at or above unsafe levels. First contactor 134 also supplies power to first transformer 150. First transformer 150 may be a 120-volt to 24-volt stepdown transformer.

First contactor 134 is also interfaced with second contactor 136. Second contactor 136 may be an auxiliary contactor, rated at 40 amps at 240 volts. Second contactor 136 creates a circuit that is normally closed. The closed circuit is deactivated by the first contactor 134 when it is energized by one of the primary monitor 102 internal relays 127, 129 upon its activation during alarm status. Second contactor 136 is used to control power to solenoid valve 140. During normal operation, gas is allowed to flow freely though solenoid valve 140 that is powered by a 120-volt circuit that is normally closed. However, when high concentrations of gas are detected and primary monitor 102 internal relays 127, 129 are activated, power is supplied to first contactor 134, thereby closing its circuit that is normally open. When this happens, power is supplied to exhaust ventilation system 138. Furthermore, when first contactor 134 is energized, it disrupts power to the circuit of second contactor 136 that is normally closed, there by breaking the circuit, closing solenoid valve 140, and disrupting gas flow.

First transformer 150 supplies 24-volt power to battery charger 152. Battery charger 152 converts the 24-volt power to 6-volts DC, which in turn supplies power to primary monitor 102. Battery charger 152 also monitors and trickle charges backup battery 156.

When power is lost (e.g., power supply 124 is cut off) during an alarm status, battery charger 152 engages battery backup 156, which supplies instantaneous backup power to primary monitor 102, remote display unit 104, primary monitor horn 110, remote display unit horn 128, primary monitor and remote display unit strobes 120 and 130, and/or exterior alarm strobe/horn unit 146.

Furthermore, when power is lost (e.g., power supply 124 is cut off) during an alarm status, exhaust ventilation system 138 is automatically shut down (in FIG. 7, a scaled version of exhaust ventilation system 138 is shown; it will be understood that the system will likely be many times larger than the one shown), despite that evacuation of the gas via this system is the primary life safety system protocol in the presence of high concentrations of dangerous gases, such as $CO_2$. Therefore, battery backup 156 may be used to: (1) maintain power to primary monitor 102, thus allowing it to continue monitoring concentration of the gas; (2) continue activation of all system horns and strobes; and (3) supply power to an optional alarm panel monitoring circuit 158, which connects the system 100 to an external monitoring service, such as a monitoring company that can alert fire and rescue, that monitors the status of the system 100. This power backup system allows the system to continue to alert occupants (including emergency responders) that harmful concentrations of the gas are present, even during power outages. It also allows the monitoring service to maintain a connection to the system to monitor the alarm status via the alarm panel monitoring circuit 158.

Second transformer 154 may supply power to exterior strobe/horn unit 146 and an actuator 160. Actuator 160 may be a 24-volt actuator, and may be used to open a sealed damper 162 to exhaust ventilation system 138 during an alarm status. Second transformer 154 may be a 120-volt to 24-volt stepdown transformer. Second transformer 154 may be wired through second contactor 136. When first contactor 134 is energized, its circuit (which is normally open) is closed, thereby mechanically closing the circuit of second contactor 136 (which is normally open) and activating actuator 160 to open damper 162 to exhaust ventilation system 138. It also activates exterior strobe/horn unit 146.

Figure 8A:
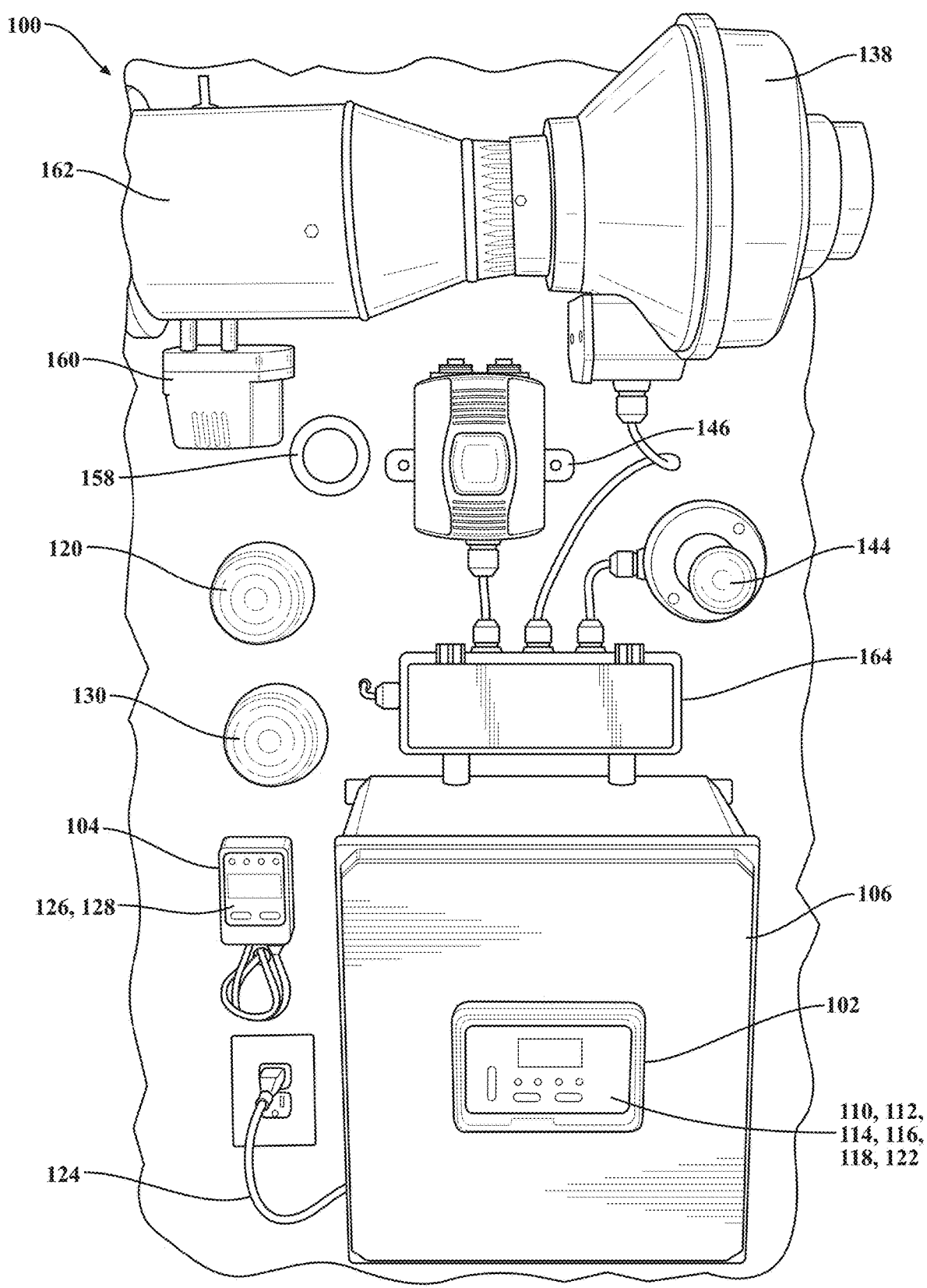
FIG. 8A is a front view of an exemplary gas monitoring and alarm system according to the third embodiment.
Figure 8B:
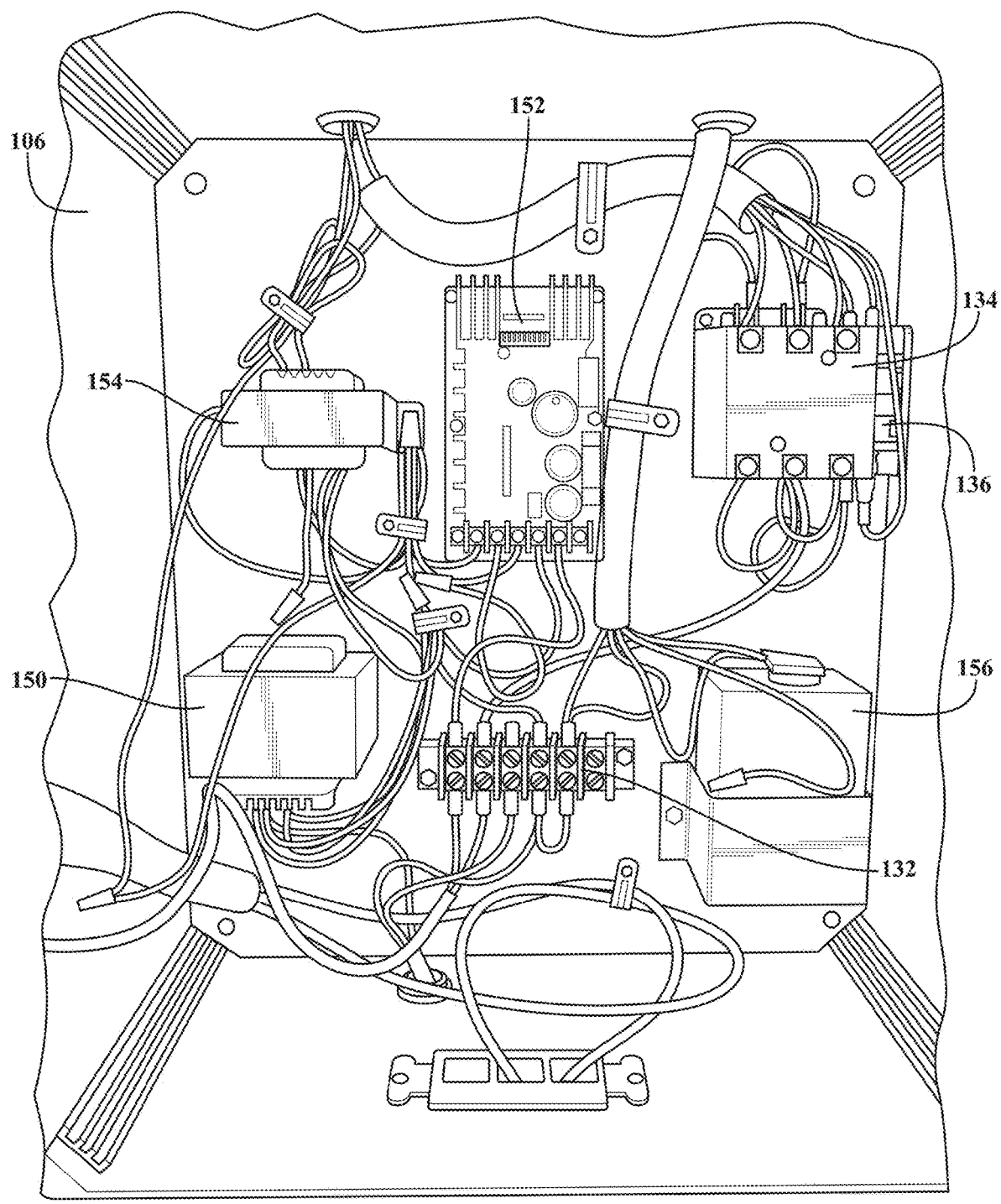
FIG. 8B is a front view of a relay interface of the gas monitoring and alarm system of FIG. 8A.

Referring now to FIGS. 8A-8B, front views of an exemplary gas monitoring and alarm system and its relay interface according to the third embodiment are illustrated. FIG. 8A further includes a terminal box 164, which may be optionally used to house wiring terminals. Additionally, as illustrated in FIG. 8A, primary monitor 102 may optionally be integrated into the front of a box/case that houses relay interface 106, rather than mounted externally to relay interface 106. FIG. 8A further shows solenoid valve indicator 142 that is included for illustration/demonstration purposes only. Solenoid valve indicator 142 represents the solenoid valve 144, normally a closed circuit. FIG. 8A further includes optional additional exterior strobe/horn unit 146 that may be used in conjunction with the existing horns/strobes of the system as an additional safety mechanism, and optional alarm panel monitoring circuit 158, both discussed above.

Relay Interface Fourth Embodiment

Figure 9:
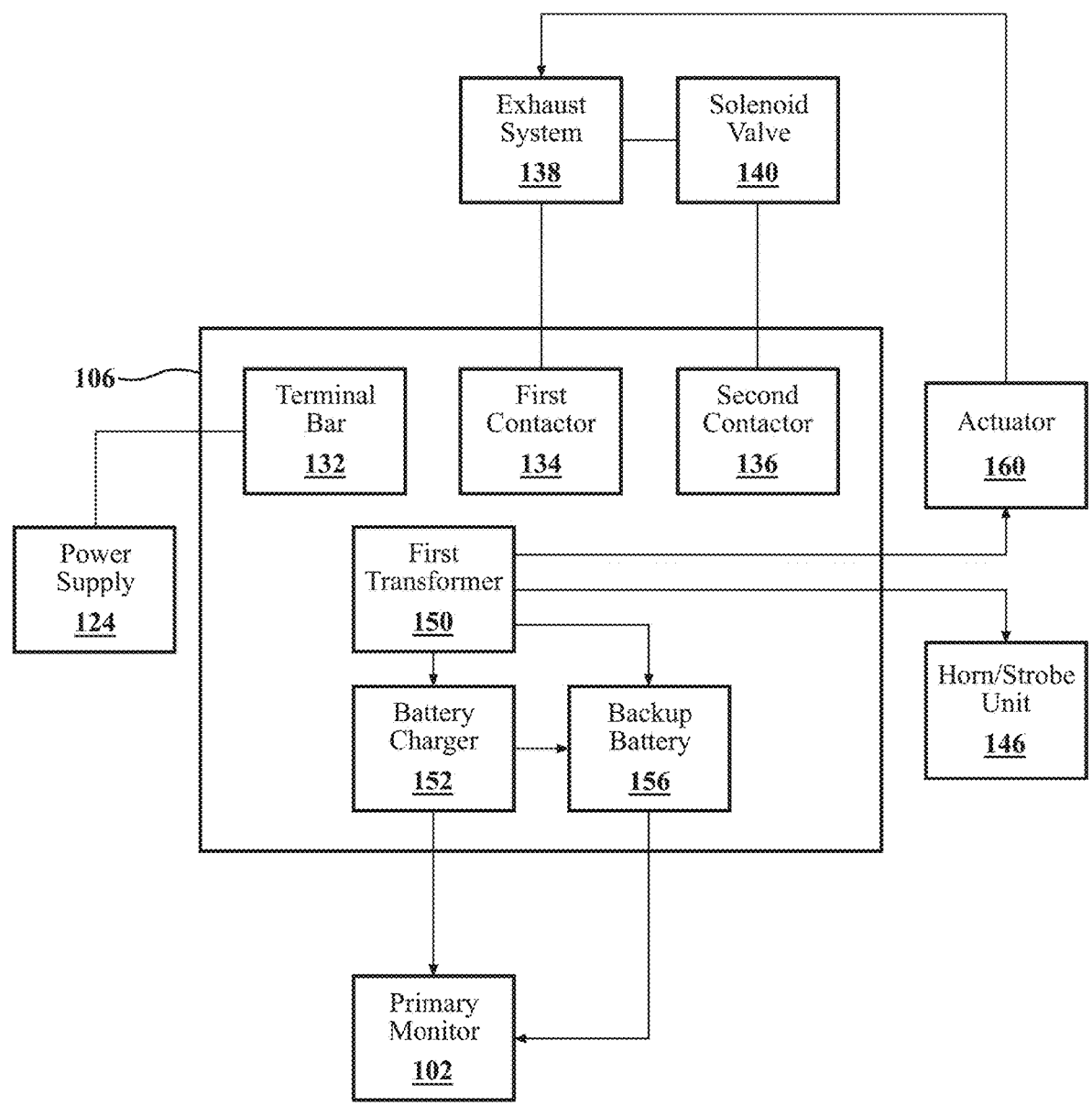
FIG. 9 is a block diagram of a relay interface of the gas monitoring and alarm system according to a fourth embodiment.

Referring now to FIG. 9, a block diagram of a relay interface of the gas monitoring and alarm system according to a fourth embodiment is shown. Relay interface 106 comprises terminal bar 132, first contactor 134, second contactor 136, a first transformer 150, a battery charger 152, and a backup battery 156.

Terminal bar 132 generates a power supply, fed from power supply 124, to deliver to first contactor 134. Terminal bar 132 and first contactor 134 together supply power to exhaust ventilation system 138 and solenoid valve 140. Terminal bar 132 also delivers power to first transformer 150 and second transformer 154.

First contactor 134 may be a 120-volt definite-purpose contactor (3 Pole), rated at 40 amps at 240 volts. First contactor 134 creates a circuit that normally open and is energized by one of the primary monitor 102 internal relays upon its activation during alarm status. When first contactor 134 is energized, it closes the circuit that supplies power to an external exhaust ventilation system 138, thereby allowing evacuation of gas when gas concentrations are at or above unsafe levels. First contactor 134 also supplies power to first transformer 150. First transformer 150 may be a 120-volt to 24-volt stepdown transformer.

First contactor 134 is also interfaced with second contactor 136. Second contactor 136 may be an auxiliary contactor, rated at 40 amps at 240 volts. Second contactor 136 creates a circuit that is normally closed. The closed circuit is deactivated by the first contactor 134 when it is energized by one of the primary monitor 102 internal relays upon its activation during alarm status. Second contactor 136 is used to control power to solenoid valve 140. During normal operation, gas is allowed to flow freely though solenoid valve 140 that is powered by a 120-volt circuit that is normally closed. However, when high concentrations of gas are detected and primary monitor 102 internal relays are activated, power is supplied to first contactor 134, thereby closing its circuit that is normally open. When this happens, power is supplied to exhaust ventilation system 138. Furthermore, when first contactor 134 is energized, it disrupts power to the circuit of second contactor 136 that is normally closed, there by breaking the circuit, closing solenoid valve 140, and disrupting gas flow.

First transformer 150 supplies 24-volt power to battery charger 152, backup battery 156, and exterior strobe/horn unit 146, and actuator 160. First transformer is wired through second contactor 136. When first contactor 134 is energized, its circuit (which is normally open) is closed, thereby mechanically closing the circuit of second contactor 136 (which is normally open) and activating actuator 160 to open damper 162 to exhaust ventilation system 138. It also activates exterior strobe/horn unit 146.

Battery charger 152 converts the 24-volt power from first transformer 150 to 24-volts DC, which in turn supplies power to primary monitor 102. Battery charger 152 also monitors and trickle charges backup battery 156. Backup battery 156 may be, for example, a 24-volt battery or two 12-volt batteries.

When power is lost (e.g., power supply 124 is cut off) during an alarm status, battery charger 152 engages battery backup 156, which supplies instantaneous backup power to primary monitor 102, remote display unit 104, primary monitor horn 110, remote display unit horn 128, primary monitor and remote display unit strobes 120 and 130, and/or exterior alarm strobe/horn unit 146.

Furthermore, when power is lost (e.g., power supply 124 is cut off) during an alarm status, exhaust ventilation system 138 is automatically shut down, despite that evacuation of the gas via this system is the primary life safety system protocol in the presence of high concentrations of dangerous gases, such as $CO_2$. Therefore, battery backup 156 may be used to: (1) maintain power to primary monitor 102, thus allowing it to continue monitoring concentration of the gas; (2) continue activation of system horns and strobes; and (3) supply power to an optional alarm panel monitoring circuit 158, which connects the system 100 to an external monitoring service, such as a monitoring company that can alert fire and rescue, that monitors the status of the system 100. This power backup system allows the system to continue to alert occupants (including emergency responders) that harmful concentrations of the gas are present, even during power outages. It also allows the monitoring service to maintain a connection to the system to monitor the alarm status via the alarm panel monitoring circuit 158.

Figure 10A:
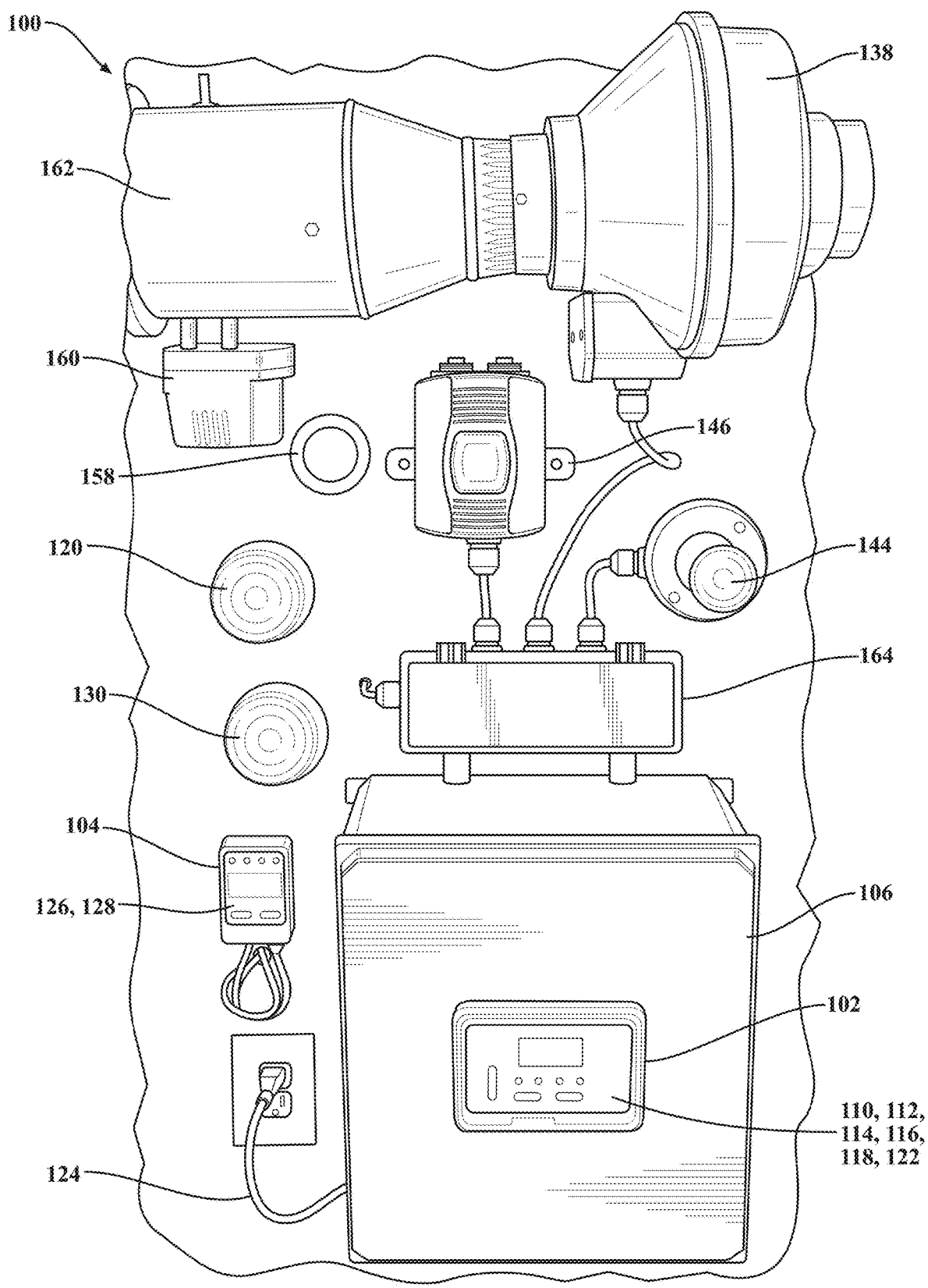
FIG. 10A is a front view of an exemplary gas monitoring and alarm system according to the fourth embodiment.
Figure 10B:
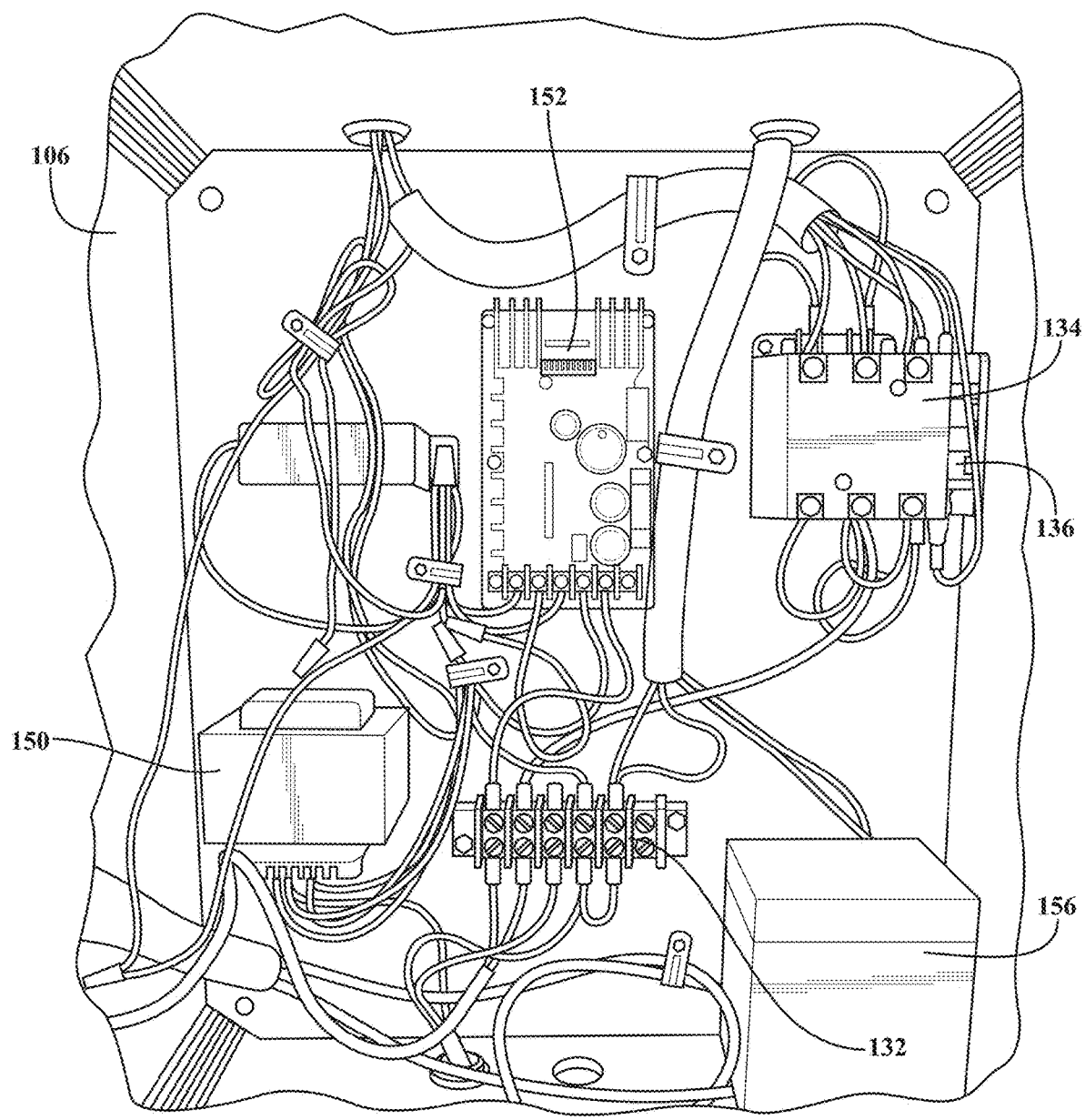
FIG. 10B is a front view of a relay interface of the gas monitoring and alarm system of FIG. 10A.

Referring now to FIGS. 10A-10B, front views of an exemplary gas monitoring and alarm system and its relay interface according to the fourth embodiment are illustrated. Optionally, the panel monitoring circuit 158 illustrated in FIG. 10A may include a data transfer system, which allows the monitoring service to read the concentration of the gas in parts per million (PPM) that is being displayed in real time on the primary monitory 102. The data transfer may be a 20 milliamp data transfer system. FIG. 10A further shows a lightbulb indicator 142 that is included for illustration/demonstration purposes only. Lightbulb 142 represents the exhaust ventilation system 138, normally a closed circuit. FIG. 10A further includes optional additional exterior strobe/horn unit 146 that may be used in conjunction with the existing horns/strobes of the system as an additional safety mechanism, and optional alarm panel monitoring circuit 158, both discussed above.

Relay Interface Fifth Embodiment

Figure 11:
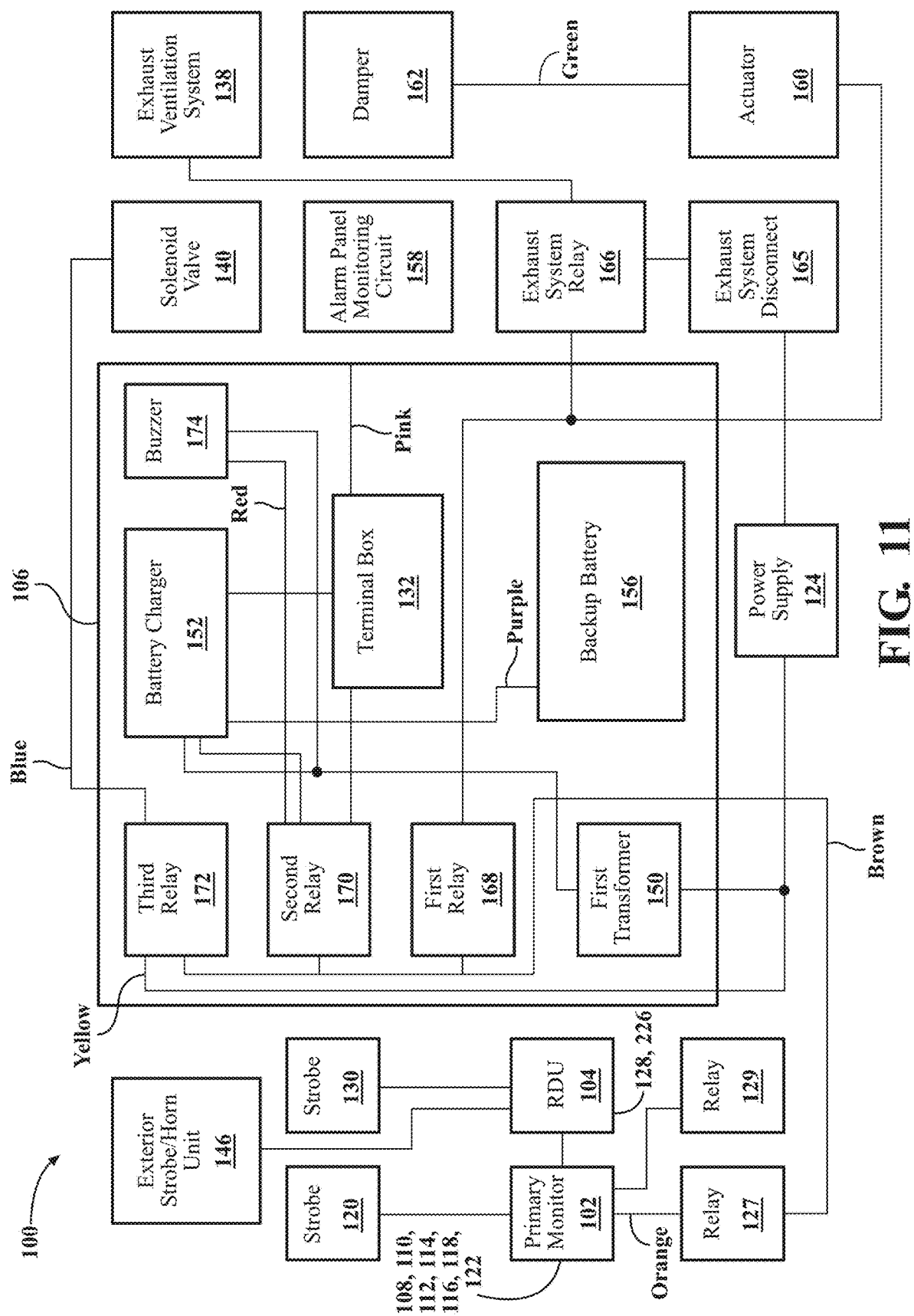
FIG. 11 is a block diagram of a relay interface of the gas monitoring and alarm system according to a fifth embodiment.

Referring now to FIG. 11, a block diagram of a relay interface of the gas monitoring and alarm system according to a fifth embodiment is shown. The sets of lines (labeled red, green, blue, pink, purple, yellow, orange, brown) show wiring connections between various components of system 100. It is contemplated that other wiring configurations would be possible.

Relay interface 106 comprises terminal bar 132, a first transformer 150, a battery charger 152, a backup battery 156, a first relay 168, a second relay 170, a third relay 172, and a buzzer 174. First, second, and third relays 168, 170, and 172 may be ice cube relays.

Terminal bar 132 receives power from power supply 124 and supplies a terminal connection location between second relay 170 and alarm panel monitoring circuit 158.

Figure 12A:
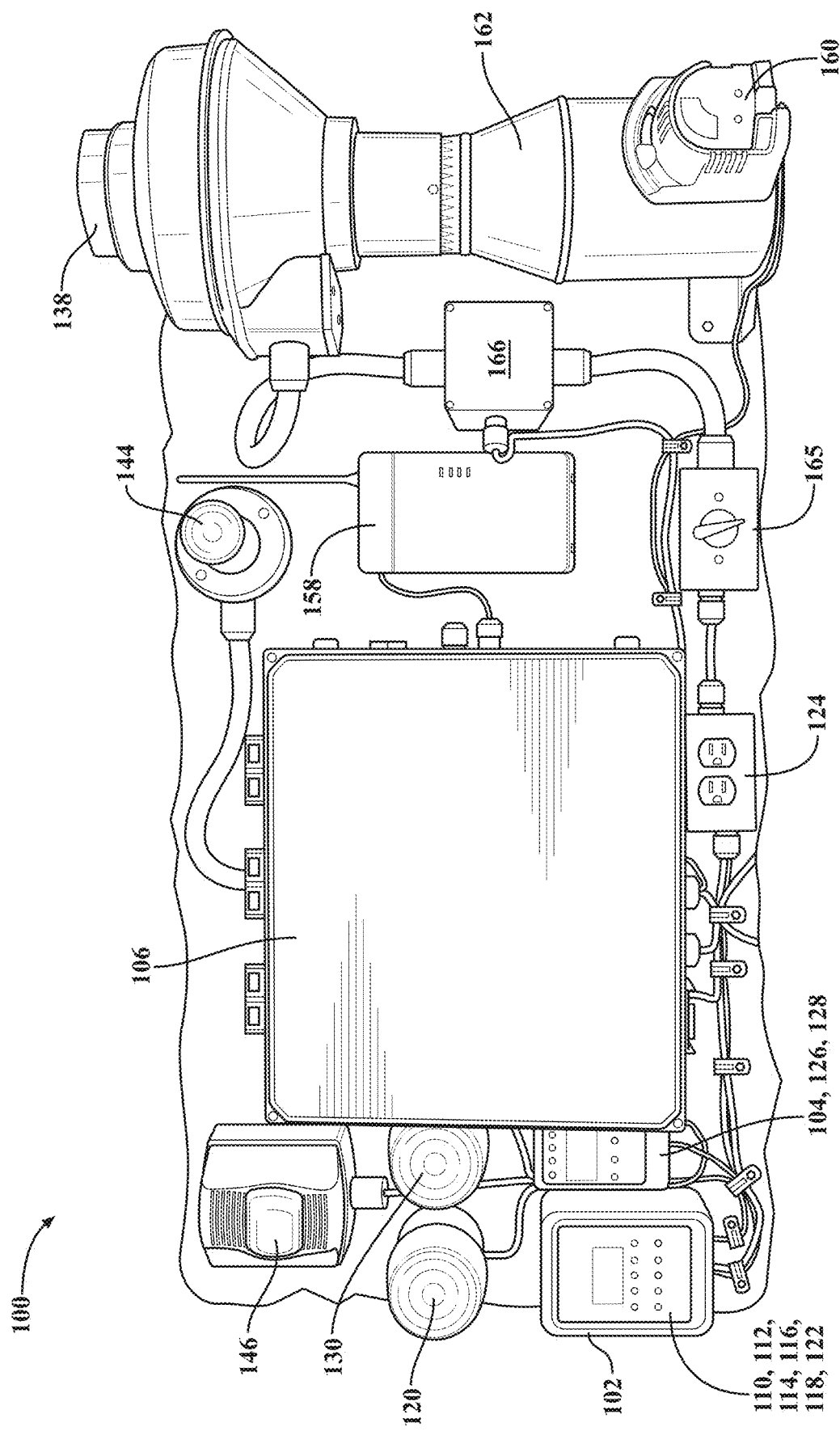
FIG. 12A is a front view of an exemplary gas monitoring and alarm system according to the fifth embodiment.

First transformer 150 may be a 120-volt to 24-volt step-down transformer that converts 24-volt AC power to 24-volts DC. First transformer 150 supplies power to primary monitor 102. It also monitors and trickle-charges backup batter 156, which may be a 24-volt battery. First transformer 150 supplies 24-volt power to battery charger 152, backup battery 156, and first, second, and third relays 168, 170, and 172. Exhaust system disconnect 165, which may be a manual circuit breaker (switch), as illustrated in FIG. 12A, is connected to exhaust system relay 166 and power supply 124.

Through first relay 168, power is supplied to actuator 160/damper 162 and an exhaust relay 166. Exhaust relay 166 is a normally open circuit. When power is supplied to exhaust relay 166, the circuit is closed, thereby supplying power to exhaust ventilation system 138.

Second relay 170 is constantly energized, which allows for simultaneous normally open circuit and normally closed circuit conditions. Constant power to second relay 170 allows for a normally closed circuit loop for alarm panel monitoring circuit 158. It also allows for a normally open circuit for buzzer 174, which may be piezoelectric.

When power is lost (e.g., power supply 124 is cut off), the normally closed circuit is opened, which sends alarm panel monitoring circuit 158 into alarm status and may, for instance, alert an external monitoring service, such as a monitoring company that can alert fire and rescue.

When power is lost (e.g., power supply 124 is cut off) during an alarm status, battery charger 152 engages battery backup 156, which supplies instantaneous backup power to primary monitor 102, remote display unit 104, primary monitor horn 110, remote display unit horn 128, primary monitor and remote display unit strobes 120 and 130, and/or exterior alarm strobe/horn unit 146.

Furthermore, when power is lost (e.g., power supply 124 is cut off) during an alarm status, exhaust ventilation system 138 is automatically shut down, despite that evacuation of the gas via this system is the primary life safety system protocol in the presence of high concentrations of dangerous gases, such as $CO_2$. Therefore, battery backup 156 may be used to: (1) maintain power to primary monitor 102, thus allowing it to continue monitoring concentration of the gas; (2) continue activation of system horns and strobes; and (3) supply power to an optional alarm panel monitoring circuit 158, which connects the system 100 to an external monitoring service, such as a monitoring company that can alert fire and rescue, that monitors the status of the system 100.

This power backup system allows the system to continue to alert occupants (including emergency responders) that harmful concentrations of the gas are present, even during power outages. It also allows the monitoring service to maintain a connection to the system to monitor the alarm status via the alarm panel monitoring circuit 158.

Additionally, backup power that is fed by backup battery 156 is triggered to supply power to the line side of second relay 170, which sends 24-volt power to buzzer 174. This produces an audible signal that house power has been lost to relay interface 106 and exhaust ventilation system 138, alerting that the system 100 is now running on 24-volt DC backup battery power.

Third relay 172 has a 24-volt powered coil but runs a normally closed 120-volt circuit that powers solenoid valve 140. In the event that house power is lost, as described above, the relay opens and power is lost to solenoid valve 140, thereby cutting off gas supply.

Figure 12B:
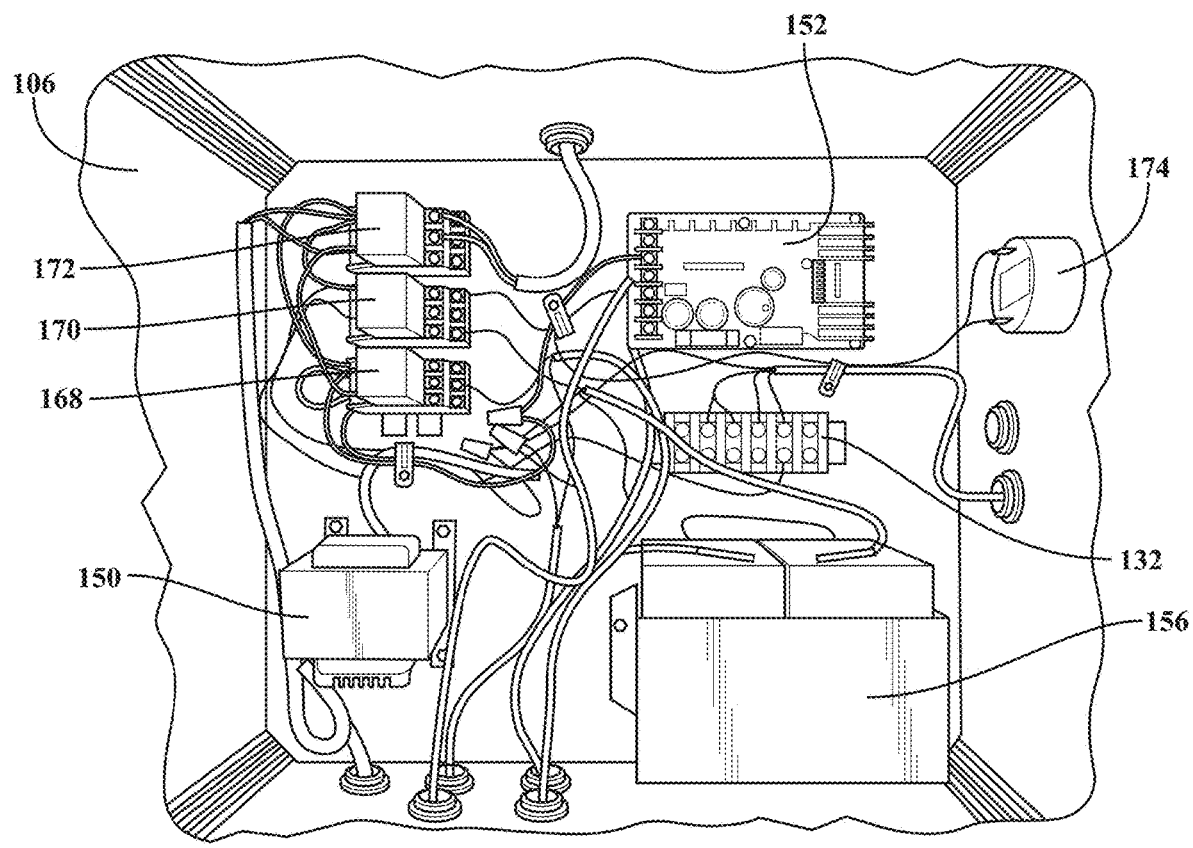
FIG. 12B is a front view of a relay interface of the gas monitoring and alarm system of FIG. 12A.

Referring now to FIGS. 12A-12B, front views of an exemplary gas monitoring and alarm system and its relay interface according to the fifth embodiment are illustrated. FIG. 12A shows a solenoid valve indicator 144 that is included for illustration/demonstration purposes only. Solenoid valve indicator 144 represents the solenoid valve 140, normally a closed circuit. FIG. 12A further includes optional additional exterior strobe/horn unit 146 that may be used in conjunction with the existing horns/strobes of the system as an additional safety mechanism, as discussed above.

Gas Monitoring and Alarm System with Master Monitor

Figure 13A:
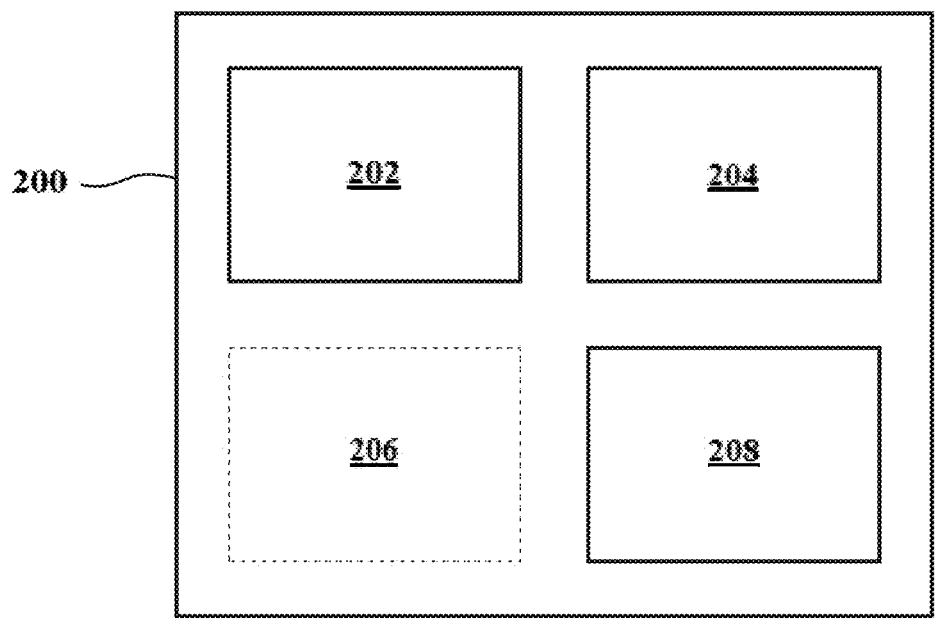
FIG. 13A is a block diagram of a gas monitoring system with a master monitor.

Referring to FIG. 13A, a block diagram of a gas monitoring and alarm with a master monitor is shown. A gas monitoring and alarm system 200 comprises a power supply 202, a master monitor 204, one or more optional slave monitors 206, and an optional alarm system 208. Master monitor 204 may be located at a source location 203. Slave monitor 206 may be located at a remote location 205. In some embodiments, there may be more than one remote location 205 if there are more than slave monitors 206 being utilized by system 200.

Figure 13B:
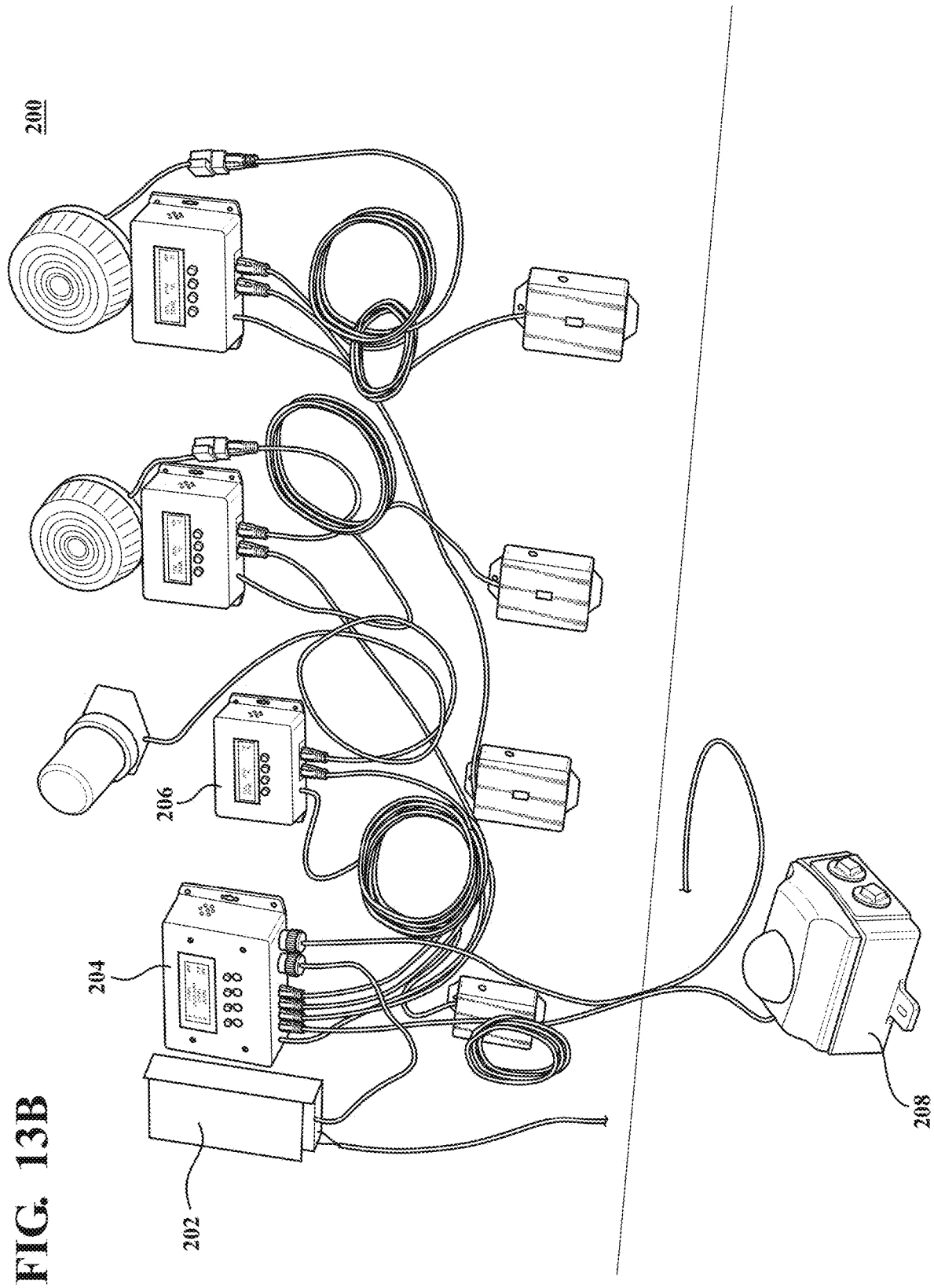
FIG. 13B is a front view of an exemplary gas monitoring system with a master monitor.

Referring now to FIG. 13B, a front view of an exemplary gas monitoring system with a master monitor is shown. Power supply 202 supplies power to master monitor 204 and optional slave monitor 206. In one embodiment, power supply 202 may be configured to supply 24V to master monitor 204. Master monitor 204 may be coupled to alarm system 208. Master monitor 204 and slave monitor 206 are discussed in detail below with reference to FIGS. 14A-E and FIGS. 15A-E, respectively.

Figure 14A:
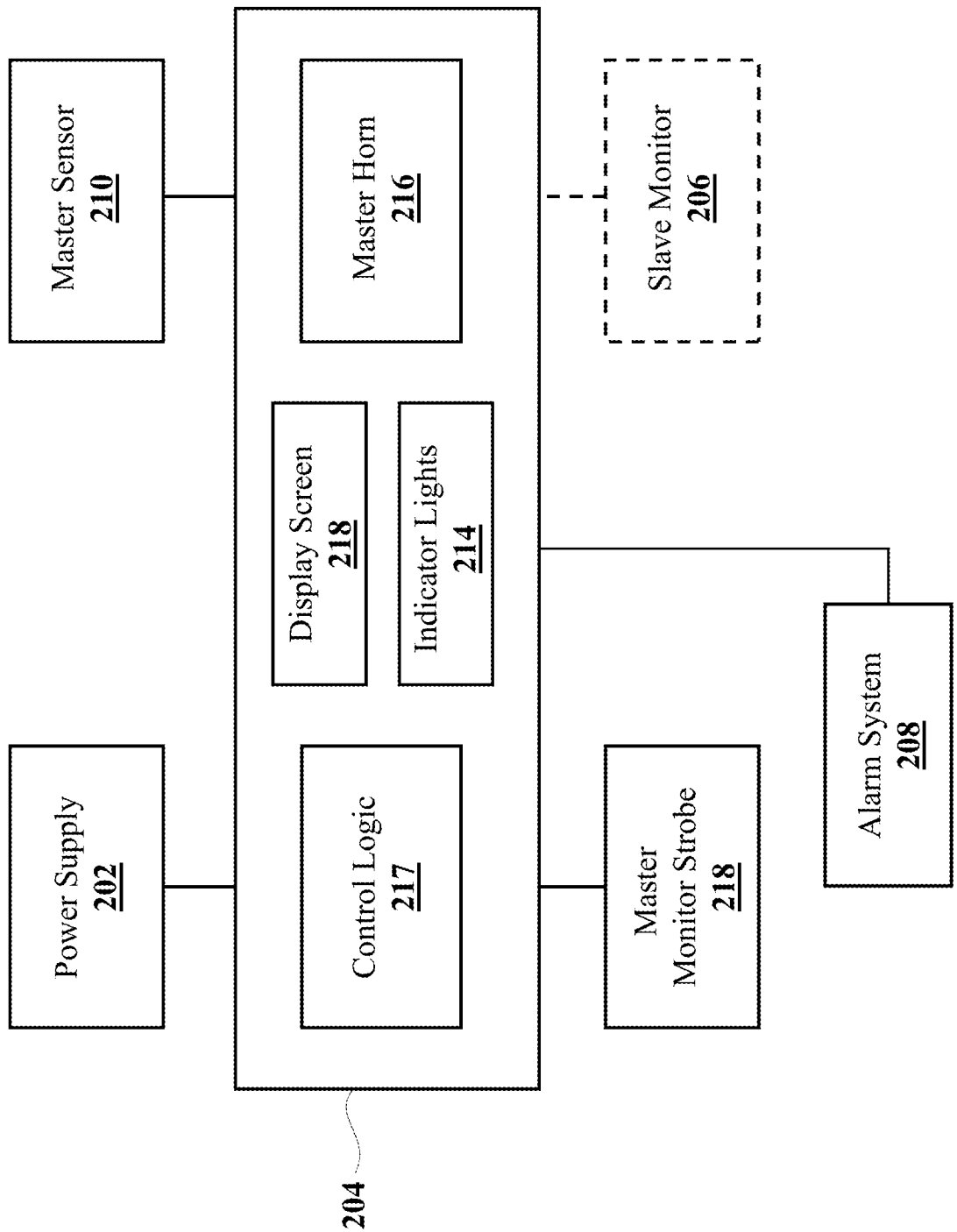
FIG. 14A is a block diagram of a master monitor of the gas monitoring system of FIGS. 13A-13B.
Figure 14B:
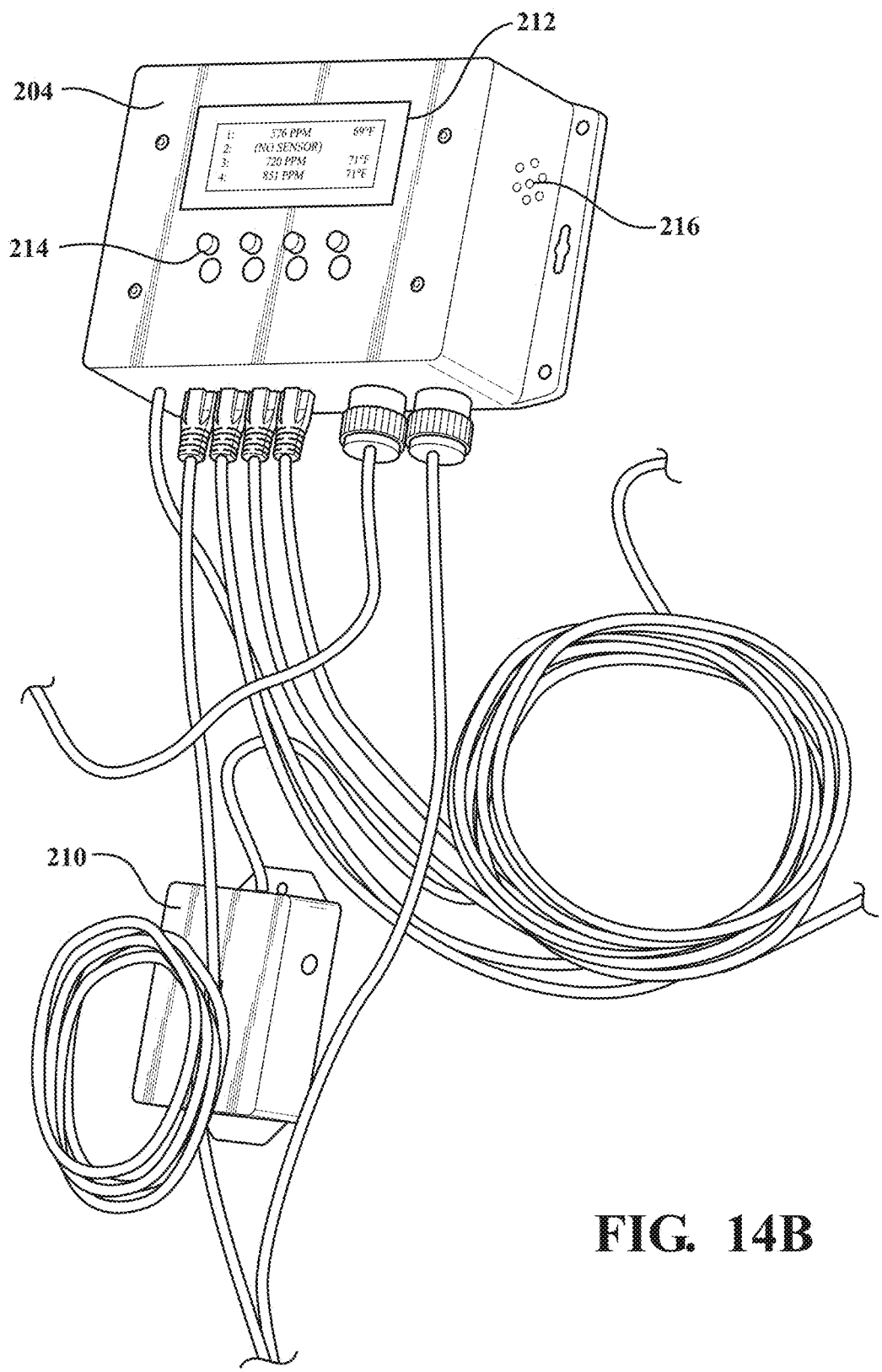
FIG. 14B is a front view of an exemplary master monitor and master monitor sensor.

Referring now to FIGS. 14A-B, a block diagram and a front view of master monitor 202 and master monitor sensor 210 of the gas monitoring system 200 of FIGS. 13A-13B are shown. Master monitor 204 receives power from power supply 202. Power supply 202 may be connected to any power source, such as a wall outlet (e.g., a 110V outlet). Power supply 202 may optionally include a backup battery to be used when the primary power source is lost (e.g., during a power outage) to send backup power to master monitor 204.

Master monitor 204 may be coupled to a master monitor sensor 210. Master monitor sensor 210 may monitor levels of gas(es) and/or other environmental conditions, such as temperature, etc. In the illustrated embodiment, master monitor sensor 210 is remote from master monitor 204. However, in other embodiments, master monitor sensor 210 may be integrated into master monitor 204. It may be desirable for master monitor sensor 210 to be remote from master monitor 204. For example, it may be desirable to keep master monitor 204 separate from an area holding a gas-containing device (e.g., a $CO_2$ tank), which would also be where master monitor sensor 210 would be kept. Master monitor 204 may act as an entry pre-warning device such that it can be conveniently observed by a person to determine whether it is safe to enter the area. By way of example and not limitation, master monitor 204 could be kept on a wall immediately outside of a closet, a walk-in cooler, etc. where the gas-containing device is located.

Master monitor 204 comprises a display screen 212, indicator lights 214, a master monitor horn 216, and a control logic 217. Display screen 212 may comprise a digital LCD screen. Display screen 212 may display information about environmental conditions and/or status of gas monitoring system 200. Master monitor horn 216 may be activated when master monitor sensor 210 senses a condition that exceeds a predefined threshold. Master monitor 204 may further be coupled to master monitor strobe 218, which may be the same or distinct from the strobe of alarm system 208. Master monitor strobe 218 may be activated when master monitor sensor 210 senses a condition that exceeds a predefined threshold. Master monitor strobe 218 may be activated simultaneously with master monitor horn 216.

Control logic 217 may be a computer, including a microprocessor, a programmable logic controller, or any other type of suitable controller for receiving sensor information and performing the operations described herein, including controlling horn/strobes 216, 218, display screen 212 and indicators 214, optionally the display of any slave monitor 206 and indicators thereof, as described in more detail below. Master monitor 204 may be coupled to alarm system 208 (e.g., by a CAT5 cable, CAT6 cable, or other Ethernet/network cable suitable to allow the master monitor 204 to communicate with the remote slave monitor 206). Alarm system 208 may be an internal or external alarm system, such as a system that includes a strobe light and/or horn, and may be remote from master monitor 204. Alarm system 208 may be activated when master monitor sensor 210 senses a condition that exceeds a predefined threshold, and/or when any connected slave monitor 206 triggers an alarm status (as discussed below). Alarm system 208 may, in some embodiments, be connected to a relay interface system (see various relay interface system embodiments, described above) that may be synced to an external monitoring service, such as a monitoring company that can alert fire and rescue services when needed, or it may be connected directly to fire and rescue services. A relay interface system may activate various safety measures to prevent or limit injury once gas levels reach an unsafe level. In yet another embodiment, alarm system 208 may not be connected to any services but may be used merely as an internal alarm system to indicate danger to those in the vicinity.

In systems that include slave monitor 206, master monitor 204 may be coupled to slave monitor 206 (e.g., by a CAT5 cable, CAT6 cable, or other Ethernet/network cable suitable to allow the master monitor 204 to communicate with the slave monitor 206). Slave monitor 206 may receive power from master monitor 204 (e.g., 24V), or may receive power from power supply 202. Slave monitor 206 may be a satellite information repeater and display the measurements made by master monitor 204. In some embodiments, slave monitor 206 may instead be controlled by a distinct controller separate from the control logic 217, such that the remote display unit controller controls the operations related to the slave monitor 206 (e.g., operation of its own display screen, indicator lights, horn/strobes, etc.). In some embodiments, the controllers of the master monitor 204 and the slave monitor(s) 206 may be in communication over a network, such as a wireless, cellular, Ethernet, or LAN network, or any other suitable network to facilitate communication between the controllers. Slave monitor 206 is discussed in more detail below with reference to FIGS. 15A-15E.

In some embodiments, master monitor 204 and/or slave monitor 206 may be capable of communicating over a wireless network such as a WiFi network, cellular, or other network which enables master monitor 204 and/or slave monitor 206 to send and receive, for example, status reports and other data to and from remote locations and devices outside of system 200.

Although the term "slave monitor" is used herein, it will be understood that a slave monitor 206 may, in some embodiments, be used as a standalone unit, while in other embodiments, the slave monitor 206 may be required to be used in connection with a master monitor 204. The terms "slave" and "remote" may be used interchangeably throughout all embodiments described herein to refer to any monitor/unit that is distinct from the "primary" or "master" monitor/unit.

Figure 14C:
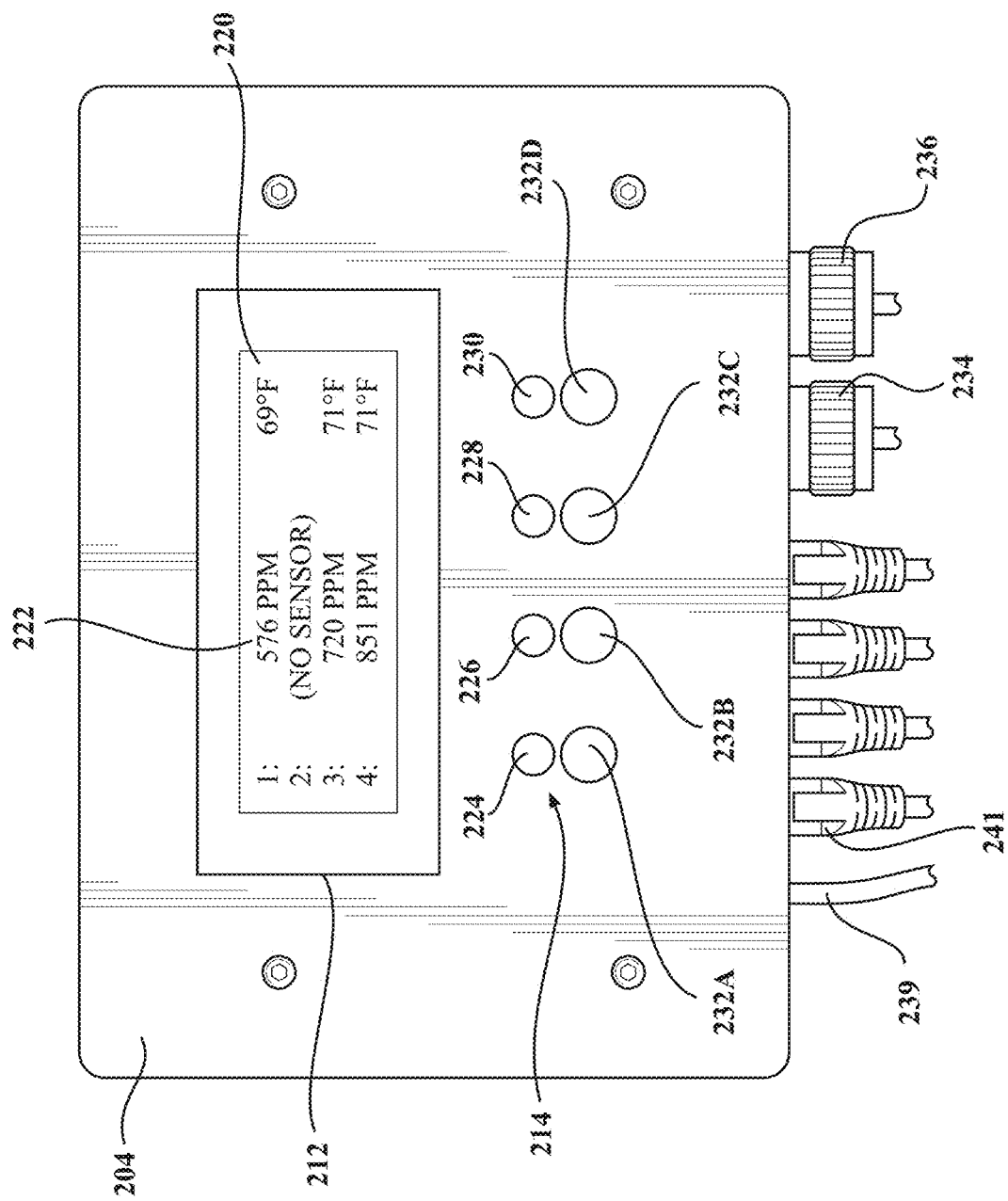
FIG. 14C is a front view of the master monitor of FIG. 14B.

Referring now to FIG. 14C, a front view of the master monitor of FIG. 14B is shown. Display screen 212 may include information about environmental conditions sensed by master monitor sensor 210. For example, display screen 212 may include a temperature indicator 220 and a gas level indicator 222. Temperature indicator 220 may indicate an ambient temperature of the room/area in which master monitor 204 and/or sensor 210 is placed. Gas level indicator 222 may indicate an ambient gas level (of any gas that is being monitored, such as, for instance, carbon dioxide or carbon monoxide) in the room/area in which master monitor 204 and/or sensor 210 is placed. It will be understood that display screen 212 may comprise other indicators for any other type of condition, including other environmental conditions, or any other relevant status information.

Master monitor indicator lights 214 may be used as a quick visual indication of the status of gas monitoring system 200. For instance, in the illustrated embodiment, master monitor indicator lights 214 comprise four indicator lights 224, 226, 228, and 230. First indicator light 224 may be a steady color (e.g., green), when gas monitoring system 200 is powered on and master monitor 204 is in a "normal" state. For example, a normal state may indicate that master monitor sensor 210 has not sensed any conditions that exceed any predefined thresholds (e.g., gas levels, temperature, etc.).

First indicator light 224 may blink and/or turn a different color (e.g., red) to indicate an alarm status. An alarm status may be triggered, for example, when master monitor sensor 210 has sensed that one or more conditions exceed a predefined threshold. In the embodiments shown herein, master monitor sensor 210 detects carbon dioxide ($CO_2$), but it will be understood that the present invention may be used to detect any gas at any concentration, or other environmental conditions (e.g., temperature). Moreover, gas monitoring system 200 may be capable of detecting multiple levels of alarm status based on user input. For example, a first alarm level may be adjustable to a first predefined concentration threshold. In one embodiment, the first predefined concentration threshold may be a concentration of $CO_2$ at 0.5% or 5,000 parts per million (PPM). A second alarm level may be adjustable to a second predefined concentration threshold. In one embodiment, the second predefined concentration threshold may be a concentration of $CO_2$ at 1.5% or 15,000 PPM. A third alarm level may be adjustable to a third predefined concentration threshold. In one embodiment, the third predefined concentration threshold may be a concentration of $CO_2$ at 3% or 30,000 PPM. However, these levels are fully customizable in increments as small as 50 PPM. Thus, the three-level alarm system may allow detection of a gas at varying concentrations, with varying responses to gas detection at each level. In some embodiments, an alarm level of master monitor 204 and/or a slave monitor 206 triggers an internal relay system, which may be coupled to a relay interface.

When master monitor 204 senses that it is connected to a slave monitor 206, first indicator light 224 may illuminate to a steady color (e.g., green). First indicator light 224 may continue to be illuminated at this color as long as it is connected to slave monitor 206.

When master monitor sensor 210 senses a gas at a concentration at or above the first predefined concentration threshold, first indicator light 224 may stay illuminated at the steady color (e.g., green), and second indicator light 226 may be illuminated an alarm status color (e.g., red) and may also blink. Master monitor horn 216 may also be activated and may emit intermittent sounds at a predefined decibel level. Master monitor strobe 218 may also be activated and may begin to flash.

If master monitor sensor 210 detects that the concentration of the gas drops below the first predefined concentration threshold, second indicator light 226 may discontinue blinking, master monitor horn 216 may discontinue sounding, and master monitor strobe 218 may discontinue flashing.

If master monitor sensor 210 detects that the concentration of the gas continues to rise above the second predefined concentration threshold, second indicator light 226 will continue to blink. Additionally, third indicator light 128 may be activated to an alarm status color (e.g., red) and may begin blinking. Master monitor horn 210 may continue sounding and master monitor strobe 218 may continue flashing, both at an increased tempo.

If master monitor sensor 210 detects that the concentration of the gas drops below the second predefined concentration and the first predefined concentration threshold, second indicator light 226 and third indicator light 228 may discontinue blinking, master monitor horn 216 may discontinue sounding, and master monitor strobe 218 may discontinue flashing. If master monitor sensor 210 detects that the concentration of the gas drops below the second predefined concentration but is still above the first predefined concentration threshold, third indicator light 228 may discontinue blinking, but second indicator light 226 may continue blinking and master monitor horn 216 continue sounding, and master monitor strobe 218 may continue flashing, until master monitor sensor 210 detects that the concentration of the gas has dropped below the first predefined concentration threshold.

If master monitor sensor 210 detects that the concentration of the gas continues to rise above the third predefined concentration threshold, second indicator light 226 and third indicator light 228 will continue to blink. Master monitor horn 210 may continue sounding and master monitor strobe 218 may continue flashing. Additionally, fourth indicator light 230 may be activated an alarm status color (e.g., red) and may begin blinking.

If master monitor sensor 210 detects that the concentration of the gas drops below the third, second, and first predefined concentration thresholds, then fourth indicator light 230, third indicator light 228, and second indicator light 226 may discontinue blinking, master monitor horn 216 may discontinue sounding, and master monitor strobe 218 may discontinue flashing. If master monitor sensor 210 detects that the concentration of the gas drops below the third predefined concentration but is still above the first and second predefined concentration thresholds, fourth indicator light 230 may discontinue blinking, but third indicator light 228 and second indicator light 226 may continue blinking and master monitor horn 216 continue sounding, and master monitor strobe 218 may continue flashing, until master monitor 210 detects that the concentration of the gas has dropped below the second and first predefined concentration thresholds.

In systems that include at least one slave monitor 206, indicator lights 214 may additionally indicate the status of slave monitor(s) 206, such that a user may be able to quickly view the status of master monitor 104 and all slave monitor(s) 206 at a glance. For instance, when master monitor 204 is in a normal state, first indicator light 224 may be a steady color (e.g., green), as described above. If a slave monitor 206 is coupled to master monitor 204, the indicator lights 224, 226 function the same as if only the master monitor sensor 210 is connected (e.g., indicator light 224 is illuminated a steady color, such as green, and indicator lights 226, 228, and 230 may be illuminated an alarm status color, such as red, if an alarm state is triggered) It will be appreciated that although the illustrated embodiments show master monitor 204 coupled to three slave monitors 206, more or fewer slave monitors 206 may be utilized. More master monitor indicator lights 214 may be included on master monitor display 212 if more slave monitors 206 are included in the system 200. If fewer than all of the available slave monitors 206 are connected or in use, then fewer than all of the available indicator lights 214 may be utilized.

In the event that an alarm status is triggered in one of the slave monitors 206, the corresponding indicator light 214 may also turn a different color (e.g., red) and/or begin blinking. Therefore, a user who is viewing master monitor 204 may be able to see that one or more monitors 204 or 206 is in a normal state while one or more of the other monitors 204/206 is in an alarm state. Master monitor 204 may be programmable to activate an alarm based on user input. For example, the user may program the system to activate an alarm on all (or select) monitors 204/206 if any one of the monitors 204/206 indicates an alarm status. Alternatively, the user may program master monitor 204 to activate an alarm only on the monitors 204/206 where the alarm status was actually triggered based on sensor data.

Master monitor display screen 212 may simultaneously display all information about all monitors 204 and/or 206 and their associated sensors (if any). For example, in the illustrated embodiment (FIG. 13B), three slave monitors 206 are connected to master monitor 204. However, the second slave monitor 206 is not connected to a sensor, and therefore no information is relayed to master monitor 204; this slave monitor 206 may be used, for example, as a repeater, displaying the level and alarm state of the master monitor 204 at a remote location. The other slave monitors 206 a relaying information to master monitor 204, including temperature and gas level (e.g., the same conditions being monitored by master monitor 204; however, in some embodiments, different conditions may be monitored by different slave monitors 206). In the illustrated embodiment (see FIG. 14C), the numeral "1" indicates information about master monitor 204, and numerals "2" through "4" indicate information about slave monitors 206, respectively. Configuration of the slave monitor(s) 206 is discussed in more detail below.

Referring again to FIG. 14C, each master monitor indicator light 214 may additionally have corresponding toggle buttons 232A-D. When pressed, toggle buttons 232A-D may display more detailed information about the monitor 204 program settings. Furthermore, if toggle buttons 232A and 232D are pressed and held simultaneously, display screen 212 may display programmable relay concentration thresholds.

Toggle buttons 232A-D may be configured to permit additional programming operations, such as a supervisor setup mode. For instance, in a supervisor setup mode, toggle buttons 232A-D may be used to change an alarm setup. In one configuration, an individual alarm mode and a common alarm mode are provided. In an individual alarm mode, alarms sound only at the unit (master monitor 204/slave monitor 206) that has detected an alarm level, and at the master monitor if the alarm is at a slave monitor. In a common alarm mode, an alarm sounds at the master monitor 204 and all connected slave monitor(s) 206, which each display a message indicating which of the connected units has raised the alarm.

Toggle buttons 232A-D may also be used to set up an averaging mode. In this mode, the system compares the lowest alarm level to the average of a preset number of hours' (e.g., eight hours) worth of sensor readings, taken at predetermined intervals (e.g., approximately once per minute). This cannot begin until the unit has accumulated at least the preset number of hours' worth of readings, and until that point, the alarm level is compared to the instantaneous reading as normal. This averaging feature can be turned off or on in supervisor mode based on the user's needs.

Toggle buttons 232A-D may also be used to configure strobe settings. For example, the strobes of the system may be programmed to activate with third alarm level only, with both the second alarm level and the third alarm level, or with all three alarm levels (alarm level one, alarm level two, and alarm level three), or any similar configurations. In some embodiments, the master monitor 204 and any slave monitors 206 will beep when any alarm level is triggered, regardless of this setting.

Toggle buttons 232A-D may also be used to configure an alarm reset mode. For example, in an automatic mode, as the gas level falls from a higher to a lower alarm level, the alarms will "step down" automatically and cancel when the gas concentration falls below the lowest alarm level. In a manual mode, the alarms will not cancel until manually reset by a user (for example, by pressing a correct combination of toggle button(s) 232A-D, such as pressing and holding toggle buttons 232A, 232B, and 232C simultaneously), system 200 is reset and all strobes and horns are discontinued from flashing/sounding. In some embodiments, the alarms cannot be reset even while in manual mode so long as there is still a gas concentration higher than one of the preset alarm levels.

First indicator light 224 may act as the system status light (e.g., normal state versus alarm state), second indicator light 226 may act as the first alarm status indicator, third indicator light 228 may act as the second alarm status indicator, and fourth indicator light 230 may act as the third alarm status indicator, all as described above with reference to master monitor 204.

Master monitor 204 may additionally comprise a number of ports for accepting connection cables. A first port 234 may accept a cable to connect master monitor 204 to power supply 202. A second port 236 may accept a cable to connect master monitor 204 to a relay interface system. In systems that include slave monitor 206, ports 238 may accept a cable or cables to connect master monitor 204 to slave monitor(s) 206. Ports 236 and 238 may accept, for example, a CAT5 cable, a CAT6 cable, or other suitable Ethernet or network cable. Additionally, a sensor port 239 may accept a cable to connect master monitor 204 to master monitor sensor 210. Sensor port 239 may accept, for example, a common phone cable or other suitable cable. A strobe port 241 may accept a cable to connect master monitor 204 to master monitor strobe 218, which may be the same or distinct from the strobe of alarm system 208.

Figure 14D:
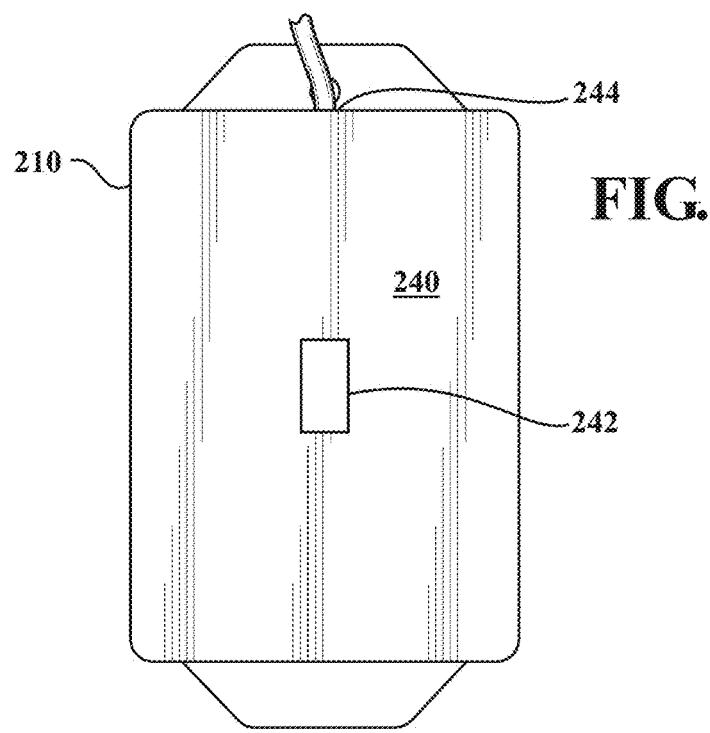
FIG. 14D is a front view of the master monitor sensor of FIG. 14B with a faceplate secured.
Figure 14E:
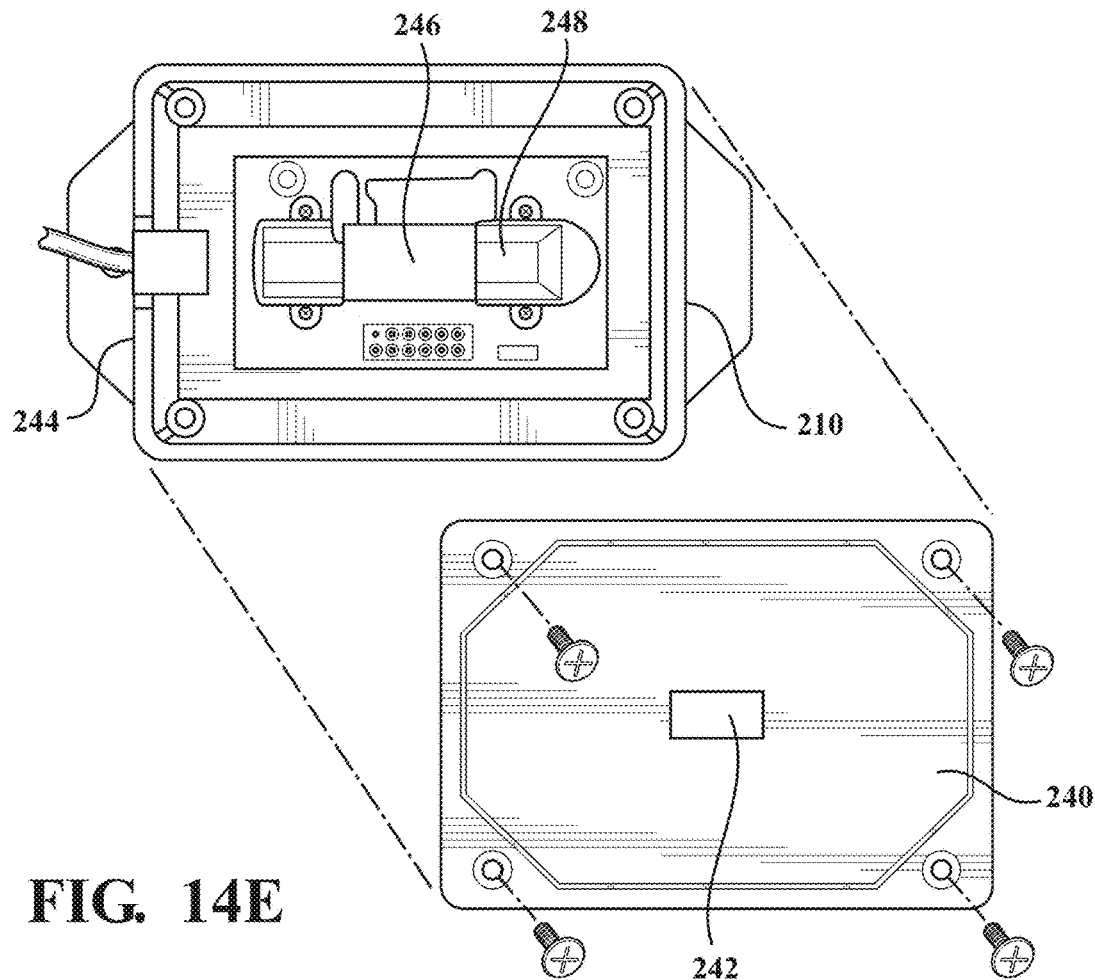
FIG. 14E is a front view of the master monitor sensor of FIG. 14D with the faceplate removed.

Referring now to FIGS. 14D-14E, front views of the master monitor sensor 210 of FIG. 14B are shown. FIG. 14D shows master monitor sensor 210 with a faceplate 240 secured. Faceplate 240 comprises an aperture 242, to allow for ambient air to flow to the sensor(s). Master monitor sensor 210 further comprises a port 244. Port 244 may accept a cable to connect master monitor sensor 210 to master monitor 204. Port 244 may accept, for example, a common phone cable or other suitable cable. FIG. 14E is a front view of the master monitor sensor 210 of FIG. 14D with faceplate 240 removed. Master monitor sensor 210 may include any number of sensors to sense any type of condition. In the illustrated embodiment, master monitor sensor 210 includes a gas sensor 246 as well as a temperature sensor 248. Gas sensor 246 may be a nondispersive infrared (NDIR) sensor or any suitable gas sensor. Master monitor sensor 210 relays information gathered from sensors 246, 248 to master monitor 204.

Figure 15A:
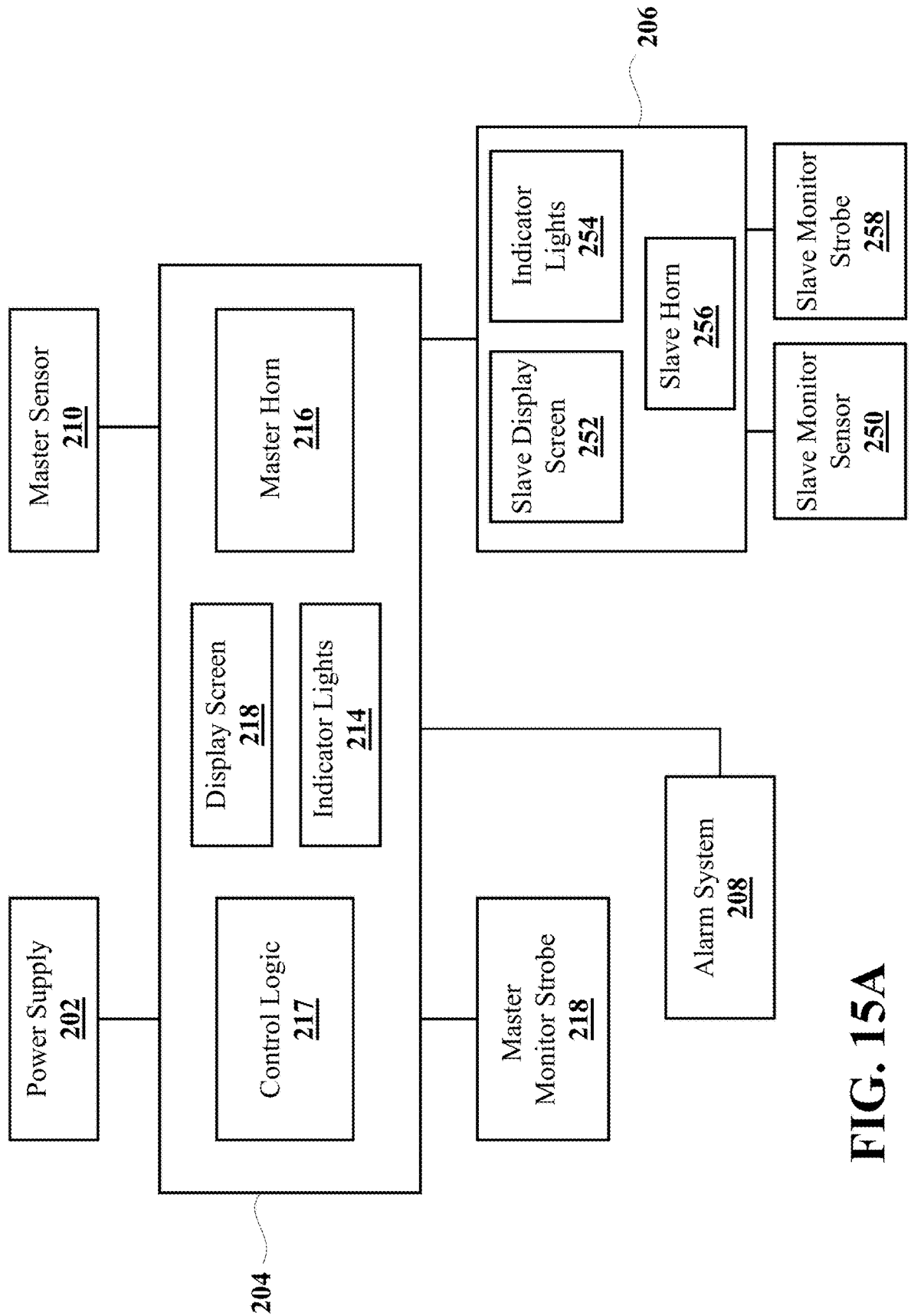
FIG. 15A is a block diagram of a master monitor and a slave monitor of the gas monitoring system of FIGS. 13A-13B.
Figure 15B:
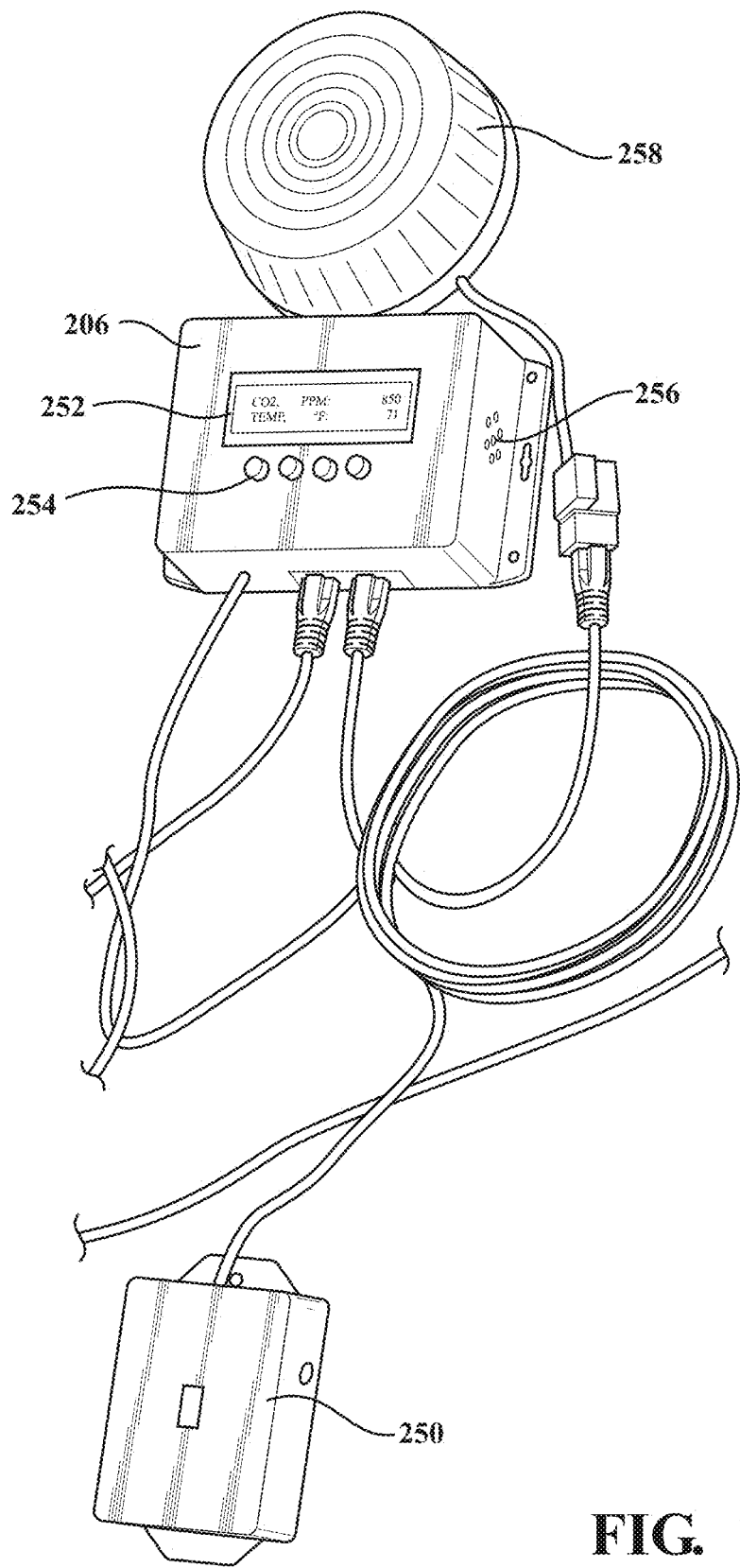
FIG. 15B is a front view of an exemplary slave monitor and slave monitor sensor.

Referring now to FIGS. 15A-15B, a block diagram and a front view of master monitor 204 and slave monitor 206 of the gas monitoring system 200 of FIGS. 13A-13B are shown. As previously discussed, slave monitor 206 is coupled to master monitor 204. In some embodiments, one slave monitor 206 may be utilized. In yet other embodiments, more than one slave monitor 206 may be utilized. For instance, in FIG. 13B, three slave monitors 206 are shown.

To connect master monitor 204 to one or more slave monitors 206, each slave monitor 206 may be assigned a unique address. For example, removable jumpers may be used to fit on pins of a circuit board to set an address of the slave monitor 206. In one embodiment, where three slave monitors 206 are possible, the following two-jumper, four-pin configuration may be used to set the address(es) of the slave monitors 206: to set a first address, no jumpers are utilized; to set a second address, one jumper is fitted to the two left pins; to set a third address, one jumper is fitted to the two right pins; to set a fourth address, both jumpers cover all four pins. It will be understood that this is only one possible configuration, described for illustrative purposes only, and is in no way limiting. Other methods or configurations for assigning a unique address to each slave monitor 206 may be used.

Referring again to FIGS. 15A-15B, master monitor 204 receives power from power supply 202 and each slave monitor 206 may receive power from master monitor 204. However, slave monitor 206 may be remote from master monitor 204 (e.g., different areas or even different rooms). In an alternate embodiment, slave monitor 206 is not connected to master monitor 204 and is instead connected to its own power source such that it may operate independently as a standalone monitor.

Each slave monitor 206 may be coupled to a slave monitor sensor 250. Slave monitor sensor 250 may monitor levels of gas(es) and/or other environmental conditions, such as temperature, etc. In the illustrated embodiment, slave monitor sensor 250 is external to slave monitor 206. However, in other embodiments, slave monitor sensor 250 may be integrated into slave monitor 206. It may be desirable for slave monitor sensor 250 to be remote from slave monitor 206.

For example, it may be desirable to keep slave monitor 206 separate from an area holding a gas-containing device (e.g., a $CO_2$ tank), which would also be where slave monitor sensor 250 would be kept. Slave monitor 206 may act as an entry pre-warning device such that it can be conveniently observed by a person to determine whether it is safe to enter the area. By way of example and not limitation, slave monitor 206 could be kept on a wall immediately outside of a gas closet or cooler where the gas-containing device is located. In other embodiments, the slave monitor 206 and the slave monitor sensor 250 may be kept in the same room/area, with the slave monitor sensor 250 mounted near the floor, where gas is likely to be concentrated, while the slave monitor 206 is mounted closer to eye-level for convenient viewing by the user.

Each slave monitor 206 comprises a slave monitor display screen 252, slave monitor indicator lights 254, and slave monitor horn 256. Slave monitor display screen 252 may comprise a digital LCD screen. Slave monitor display screen 252 may display information about environmental conditions and/or status of slave monitor sensor 250. Slave monitor horn 256 may be activated when slave monitor sensor 250 senses a condition that exceeds a predefined threshold. Slave monitor 206 may further be coupled to slave monitor strobe 258. Slave monitor strobe 258 may be activated when slave monitor sensor 250 senses a condition that exceeds a predefined threshold.

Figure 15C:
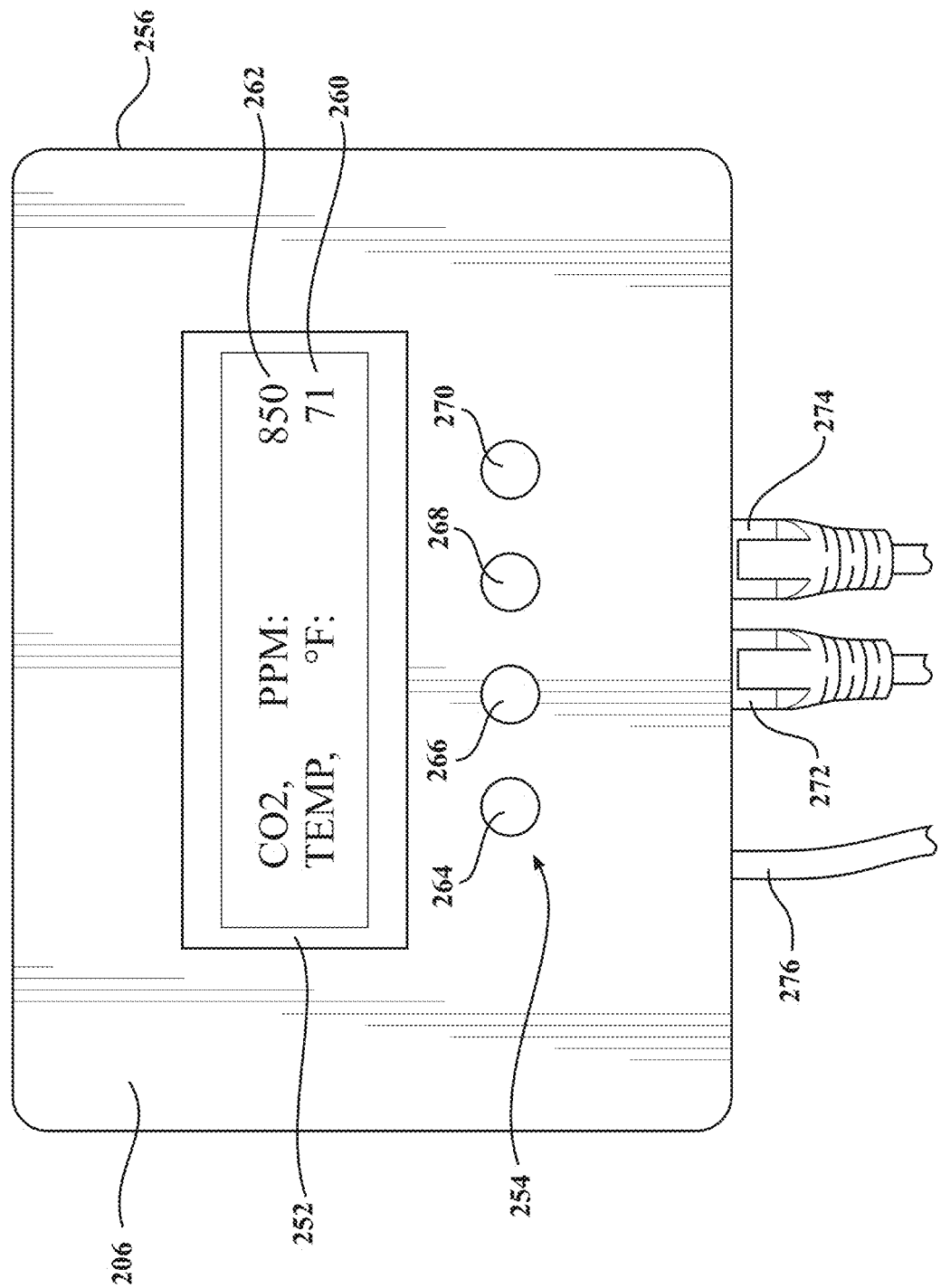
FIG. 15C is front view of the slave monitor of FIG. 15B.

Referring now to FIG. 15C, a front view of the slave monitor of FIG. 15B is shown. Slave monitor display screen 252 may include information about environmental conditions sensed by slave monitor sensor 250. For example, slave monitor display screen 252 may include a temperature indicator 260 and a gas level indicator 262. Temperature indicator 260 may indicate an ambient temperature of the room/area in which slave monitor sensor 250 is placed. Gas level indicator 1262 may indicate an ambient gas level (of any gas that is being monitored, such as, for instance, carbon dioxide) in the room/area in which slave monitor sensor 250 is placed. It will be understood that slave monitor display screen 252 may comprise other indicators for any other type of condition, including other environmental conditions, or any other relevant status information.

Slave monitor indicator lights 254 may be used as a quick visual indication of the status of slave monitor 206. For instance, in the illustrated embodiment, slave monitor indicator lights 254 comprise four indicator lights 264, 266, 268, and 270. First indicator light 264 may be a steady color (e.g., green), when slave monitor 206 is powered on and in a "normal" state. For example, a normal state may indicate that slave monitor sensor 250 has not sensed any conditions that exceed any predefined thresholds (e.g., gas levels, temperature, etc.).

Second indicator light 266 may blink (e.g., red) to indicate an alarm status. An alarm status may be triggered, for example, when slave monitor sensor 250 has sensed that one or more conditions exceed a predefined threshold. In the embodiments shown herein, slave monitor sensor 250 detects carbon dioxide ($CO_2$), but it will be understood that the present invention may be used to detect any gas at any concentration, or other environmental conditions (e.g., temperature).

As previously discussed, gas monitoring system 200 may be capable of detecting multiple levels of alarm status based on user input. For example, a first alarm level may be adjustable to a first predefined concentration threshold, a second alarm level may also be adjustable to a second predefined concentration threshold, and a third alarm level may be adjustable to a third predefined concentration threshold.

When slave monitor sensor 250 senses a gas at a concentration at or above the first predefined concentration threshold, second indicator light 266 may blink an alarm status color (e.g., red) and master second indicator light 226 may also blink an alarm status color (e.g., red). Slave monitor horn 256 may also be activated and may emit intermittent sounds at a predefined decibel level. Slave monitor strobe 258 may also be activated and may begin to flash.

If slave monitor sensor 250 detects that the concentration of the gas drops below the first predefined concentration threshold, second indicator light 266 may discontinue blinking, slave monitor horn 256 may discontinue sounding, and slave monitor strobe 258 may discontinue flashing. First indicator light 264 may stay illuminated at the normal state color (e.g., steady green) so long as there is a connection between the master monitor 204 and the slave monitor 206.

If slave monitor sensor 250 detects that the concentration of the gas continues to rise above the second predefined concentration threshold, third indicator light 268 and master third indicator light 228 will begin to blink an alarm status color (e.g., red). Slave monitor horn 256 may continue sounding and slave monitor strobe 258 may continue flashing, both at an increased tempo. Additionally, indicator light 226 may continue blinking.

If slave monitor sensor 250 detects that the concentration of the gas drops below the second predefined concentration and the first predefined concentration threshold, second indicator light 266 and third indicator light 268, as well as master second indicator light 226 and master third indicator light 228, may discontinue blinking, slave monitor horn 256 may discontinue sounding, and slave monitor strobe 258 may discontinue flashing. First indicator light 264 may stay illuminated at the normal state color (e.g., steady green) so long as there is a connection between the master monitor 204 and the slave monitor 206.

If slave monitor sensor 250 detects that the concentration of the gas continues to rise above the third predefined concentration threshold, second indicator light 266 and third indicator light 268, as well as master second indicator light 226 and master third indicator light 228, will continue to blink the alarm status color (e.g., red). Additionally, fourth indicator light 270, as well as master fourth indicator light 230, may be activated and may begin blinking an alarm status color (e.g., red). Slave monitor horn 1256 may continue sounding and slave monitor strobe 258 may continue flashing.

If slave monitor sensor 250 detects that the concentration of the gas drops below the third, second, and first predefined concentration thresholds, then fourth indicator light 270, third indicator light 268, and second indicator light 266 may discontinue blinking, slave monitor horn 256 may discontinue sounding, and slave monitor strobe 258 may discontinue flashing. First indicator light 264 may return to the normal state color (e.g., steady green).

Slave monitor 206 may additionally comprise a number of ports for accepting connection cables. A first port 272 may accept a cable to connect slave monitor 206 to master monitor 204. A second port 274 may accept a cable to connect slave monitor 206 to slave monitor strobe 258. First and second ports 272, 274 may accept, for example, a CAT5 cable or other suitable cable. A third port 276 may accept a cable to connect slave monitor 206 to slave monitor sensor 250. Third port 276 may accept, for example, a common phone cable or other suitable cable.

Figure 15D:
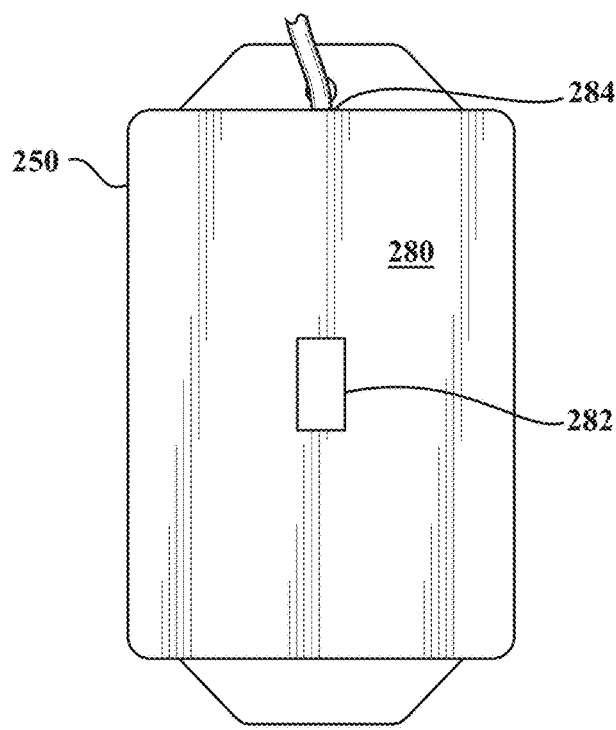
FIG. 15D is a front view of the slave monitor sensor of FIG. 15B with a faceplate secured.
Figure 15E:
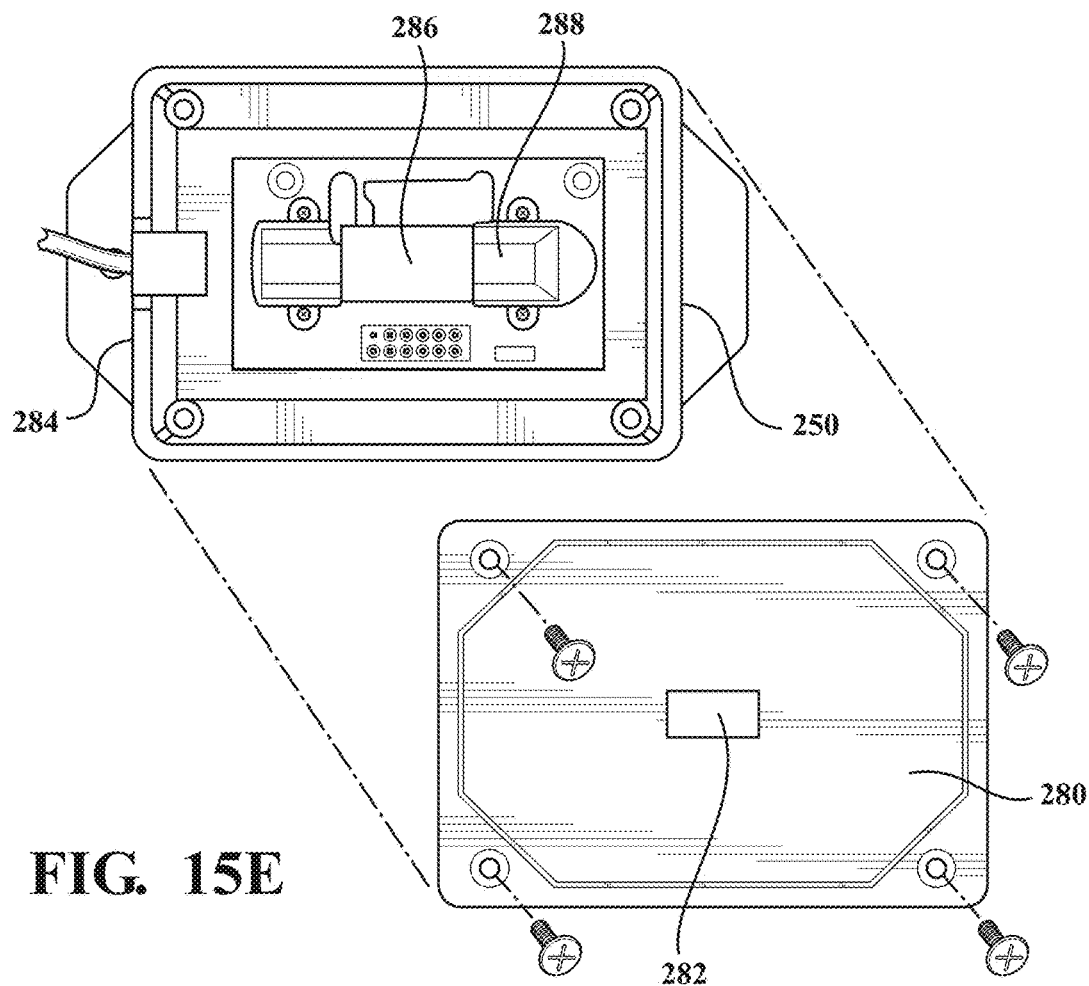
FIG. 15E is a front view of the slave monitor sensor of FIG. 15D with the faceplate removed.

Referring now to FIGS. 15D-15E, front views of the slave monitor sensor 250 of FIG. 15B are shown. FIG. 15D shows slave monitor sensor 250 with a faceplate 280 secured. Faceplate 280 comprises an aperture 282, to allow for ambient air to flow to the sensor(s). Slave monitor sensor 250 further comprises a port 284. Port 284 may accept a cable to connect slave monitor sensor 250 to slave monitor 206. Port 284 may accept, for example, a common phone cable or other suitable cable. FIG. 15E is a front view of the slave monitor sensor 250 of FIG. 15D with faceplate 280 removed. Slave monitor sensor 250 may include any number of sensors to sense any type of condition. In the illustrated embodiment, slave monitor sensor 250 includes a gas sensor 286 as well as a temperature sensor 288. Gas sensor 286 may be a nondispersive infrared (NDIR) sensor or any suitable gas sensor. Slave monitor sensor 250 relays information gathered from sensors 286, 288 to slave monitor 206. In turn, slave monitor 206 relays all gathered information to master monitor 204.

In some embodiments, master monitor 204 and/or slave monitor(s) 206 may additionally include a real-time clock and/or may be configured to log the date and/or time of any alarms that are triggered, which may be useful for reporting or inspection purposes.

Gas Monitoring and Alarm System

Figure 16:
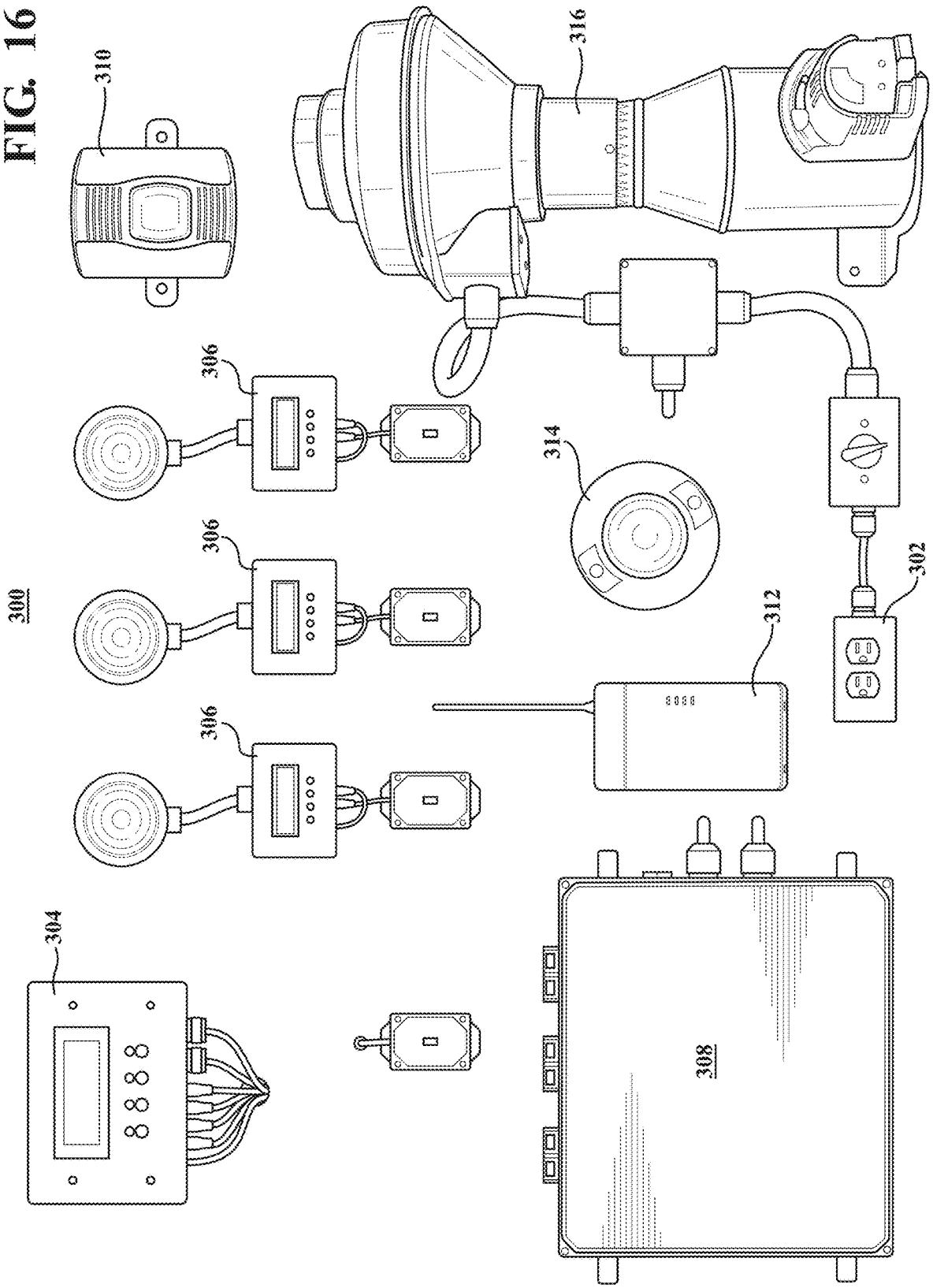
FIG. 16 is a front view of an exemplary gas monitoring system.

Referring now to FIG. 16, a front view of an exemplary gas monitoring system 300 is shown. Power supply 302 may supply power to master monitor 304 and/or one or more slave monitors 306. In one embodiment, power supply 302 may be configured to supply 24V to master monitor 304. Master monitor 304 and slave monitor 306 may each be coupled to sensors (e.g., gas/temperature sensors) and may be similar to master monitor 204 and slave monitor 206, as discussed in detail above with reference to FIGS. 14A-E and FIGS. 15A-E, respectively.

Referring again to FIG. 16, the system 300 may include relay interface 308, which may be similar to any of the embodiments of relay interfaces described with reference to FIG. 3, 5, 7, or 9 herein.

The system 300 may further include additional exterior strobe/horn unit 310 that may be used in conjunction with the existing horns/strobes of the system as an additional safety mechanism, and optional alarm panel monitoring circuit 312. Both of these components are described in more detail above, with respect to FIGS. 8A and 7, respectively. In some embodiments, one or more of the alarm strobes of the system 300 may be daisy chained.

The system 300 may further include an exhaust ventilation system 316. External exhaust ventilation indicator 314 is shown in FIG. 16 for illustration/demonstration purposes only. External exhaust ventilation system indicator 314 represents the exhaust ventilation system 316, normally an open circuit. Exhaust ventilation system 316 may be similar to the exhaust ventilation system 138 described above, for example, with reference to FIGS. 5, 7, 8A, 9, 10A, 11, and 12A.

It will be understood that the primary/master monitors and the remote/slave monitors of the systems described herein may be fully programmable and customizable to suit the user's needs. For instance, specific alarm responses and alarm levels that differ from the embodiments described above may be programmed based on the user's particular needs. The example alarm responses/levels are provided for illustrative purposes and are not meant to be restrictive. Additionally, it will be understood that any combination of any of the components of the systems described herein may be used to provide a customized gas monitoring and/or alarm system according to the user's needs. For instance, the number of monitors (either primary/master or slave/remote) may vary, and some components, such as a relay interface and external exhaust ventilation system, may be included or omitted from a system based on the user's needs. The various combinations of components if the embodiments of the systems described herein are provided for illustrative purposes and are not meant to be restrictive.

Gas Monitoring and Alarm Methods

Figure 17:
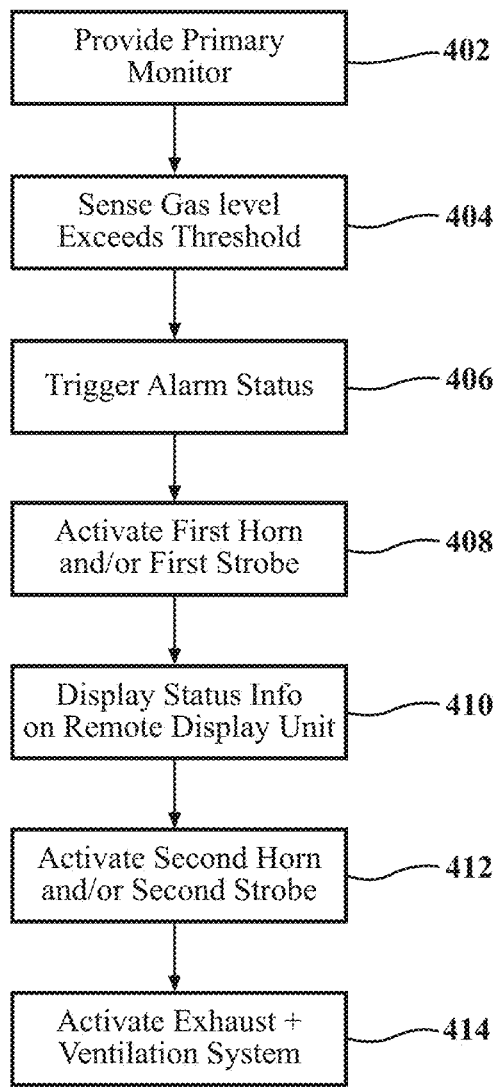
FIG. 17 is a flow diagram illustrating a first method for monitoring gas levels and triggering an alarm system.

Referring now to FIG. 17, a flow diagram illustrating a first method 400 for monitoring gas levels and triggering an alarm system is shown. At a first step 402, a primary monitor (e.g., primary monitor 102) is provided. The primary monitor is configured to monitor a concentration of a gas in an area. At a second step 404, a sensor of the primary monitor (e.g., gas sensor 108) senses that the concentration of the gas exceeds a predefined alarm threshold. At a third step 406, the primary monitor triggers an alarm status. At a fourth step 408, the primary monitor activates at least one of a first strobe (e.g., primary monitor strobe 120) and a first horn (e.g., primary monitor horn 110). At a fifth step 410, information related to the concentration of the gas and the alarm status is displayed on a remote display unit (e.g., remote display unit 104) communicatively coupled to the primary monitor. At a sixth step 412, the remote display unit activates at least one of a second strobe (e.g., remote display unit strobe 130) and a second horn (e.g., remote display unit horn 128) when the alarm status is triggered. At a seventh step 414, a relay interface (e.g., relay interface 106) communicatively coupled to the primary monitor activates an exhaust and ventilation system (e.g., external exhaust ventilation system 138) configured to evacuate the gas from the area.

Figure 18:
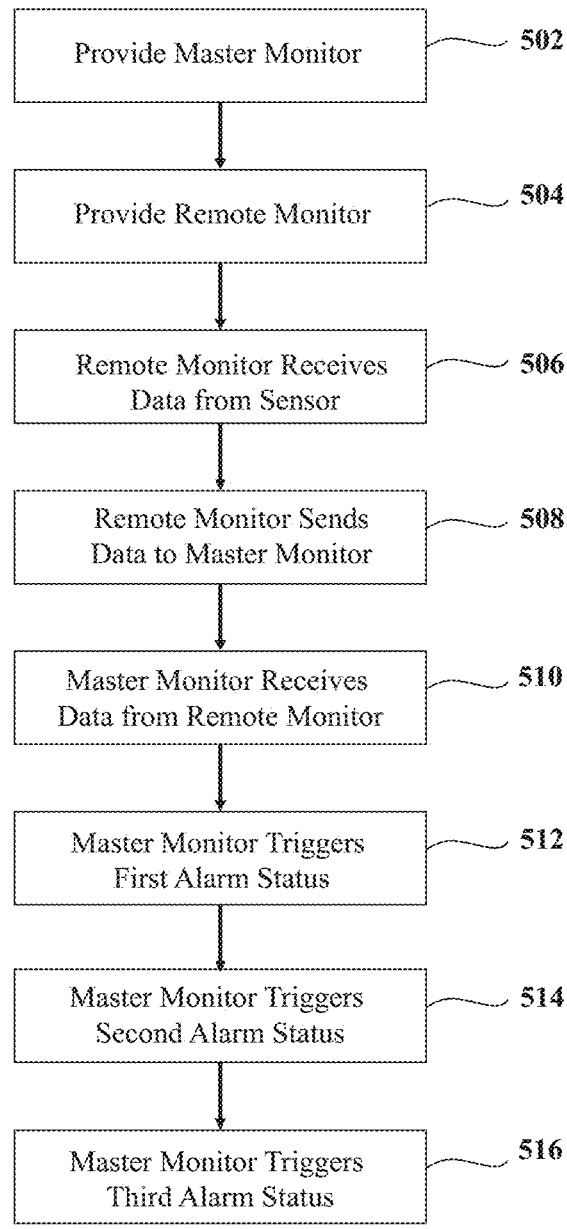
FIG. 18 is a flow diagram illustrating a second method for monitoring gas levels and triggering an alarm system.

Referring now to FIG. 18, a flow diagram illustrating a second method 500 for monitoring gas levels and triggering an alarm system is shown. At a first step 502, a master monitor (e.g., master monitor 204 or 304) is provided. The master monitor is coupled to a master sensor (e.g., sensor 210). The master sensor is configured to sense a concentration of a gas in a first area and send data about the concentration of the gas to the master monitor. At a second step 504, at least one remote monitor (e.g., slave monitor 206 or 306) communicatively coupled to the master monitor is provided. The at least one remote monitor is coupled to a remote sensor (e.g., slave monitor sensor 250) configured to sense a concentration of gas in a second area. At a third step 506, the at least one remote monitor receives data about the concentration of the gas in the second area from the remote sensor. At a fourth step 508, the at least one remote monitor sends the data to the master monitor. At a fifth step 510, the master monitor receives the data from the at least one remote monitor. At a sixth step 512, the master monitor triggers a first alarm status when the concentration of gas in at least one of the first area and the second area exceeds a first predefined alarm threshold. At a seventh step 514, the master monitor triggers a second alarm status when the concentration of gas in at least one of the first area and the second area exceeds a second predefined alarm threshold. At an eighth step 516, the master monitor triggers a third alarm status when the concentration of gas in at least one of the first area and the second area exceeds a third predefined alarm threshold.

Although the figures may include particular components (e.g., brands and/or product types) for illustration purposes, it is understood that such components may comprise any brand or product type with comparable specifications.

It is to be appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A gas monitoring and alarm system comprising:
a master monitor coupled to a master sensor, the master sensor configured to sense a concentration of a gas in a first area and send data about the concentration of the gas to the master monitor;
at least one remote monitor communicatively coupled to the master monitor, the at least one remote monitor coupled to a remote sensor configured to sense a concentration of gas in a second area, the at least one remote monitor configured to:
receive data about the concentration of the gas in the second area from the remote sensor, and
send the data to the master monitor, and wherein the master monitor is further configured to:
trigger a second alarm status when the concentration of gas in at least one of the first area and the second area exceeds a second predefined alarm threshold, wherein the second predefined alarm threshold is larger than the first predefined alarm threshold; and
trigger a third alarm status when the concentration of gas in at least one of the first area and the second area exceeds a third predefined alarm threshold, wherein the third predefined alarm threshold is larger than the first predefined alarm threshold and the second predefined threshold;
a relay interface system coupled to the master monitor;
an exhaust and ventilation system external coupled to the relay interface system;
an alarm panel monitoring circuit coupled to the relay interface system, wherein the alarm panel monitoring circuit is connected to an external monitoring service;
wherein the relay interface system is configured to activate the exhaust and ventilation system during the third alarm status,
wherein the alarm panel monitoring circuit is configured to send an alert to the external monitoring service during the alarm status; and
wherein the exhaust and ventilation system is configured to evacuate gas from at least one the first area and the second area.

2. The gas monitoring and alarm system of claim 1, wherein the master monitor is further configured to activate at least one of an alarm indicator light, a strobe, and a horn when the alarm status is triggered.

3. The gas monitoring and alarm system of claim 1, wherein the remote monitor is further configured to activate at least one of an alarm indicator light, a strobe, and a horn when the alarm status is triggered.

4. The gas monitoring and alarm system of claim 1, wherein the first predefined alarm threshold is a concentration of 5,000 parts per million of carbon dioxide.

5. The gas monitoring and alarm system of claim 1, wherein the second predefined alarm threshold is a concentration of 15,000 parts per million of carbon dioxide.

6. The gas monitoring and alarm system of claim 1, wherein the third predefined alarm threshold is a concentration of 30,000 parts per million of carbon dioxide.

7. The gas monitoring and alarm system of claim 1, wherein the master monitor is further configured to activate at least one of a second alarm indicator light, a second strobe, and a second horn when the second alarm status is triggered.

8. The gas monitoring and alarm system of claim 1, wherein the at least one remote monitor is further configured to activate at least one of a second alarm indicator light, a second strobe, and a second horn when the second alarm status is triggered.

9. The gas monitoring and alarm system of claim 1, wherein at least one of the master monitor and the remote monitor is configured to connect to a wireless network.

10. A method for monitoring gas levels and triggering an alarm system, the method comprising:
providing a master monitor coupled to a master sensor, the master sensor configured to sense a concentration of a gas in a first area and send data about the concentration of the gas to the master monitor;
providing at least one remote monitor communicatively coupled to the master monitor, the at least one remote monitor coupled to a remote sensor configured to sense a concentration of gas in a second area;
receiving, by the at least one remote monitor, data about the concentration of the gas in the second area from the remote sensor,
sending, by the at least one remote monitor, the data to the master monitor,
receiving, by the master monitor, the data from the at least one remote monitor, and
triggering, by the master monitor, a first alarm status when the concentration of gas in at least one of the first area and the second area exceeds a first predefined alarm threshold;
triggering a second alarm status when the concentration of gas in at least one of the first area and the second area exceeds a second predefined alarm threshold, wherein the second predefined alarm threshold is larger than the first predefined alarm threshold;
triggering a third alarm status when the concentration of gas in at least one of the first area and the second area exceeds a third predefined alarm threshold, wherein the third predefined alarm threshold is larger than the first predefined alarm threshold and the second predefined threshold;
providing a relay interface system coupled to the master monitor;
providing an exhaust and ventilation system external coupled to the relay interface system;
providing an alarm panel monitoring circuit coupled to the relay interface system, wherein the alarm panel monitoring circuit is connected to an external monitoring service;
activating, by the relay interface system, the exhaust and ventilation system during the third alarm status; and
sending, by the alarm panel monitoring circuit, an alert to the external monitoring service during the alarm status; and
evacuating, by the exhaust and ventilation system is configured, gas from at least one of the first area and the second area.

11. The method of claim 10, further comprising activating, by the master monitor, at least one of an alarm indicator light, a strobe, and a horn when the first alarm status is triggered.

12. The method of claim 10, further comprising activating, by the remote monitor, at least one of an alarm indicator light, a strobe, and a horn when the first alarm status is triggered.

13. The method of claim 10, wherein the first predefined alarm threshold is a concentration of 5,000 parts per million of carbon dioxide.

14. The method of claim 10, wherein the second predefined alarm threshold is a concentration of 15,000 parts per million of carbon dioxide.

15. The method of claim 10, wherein the third predefined alarm threshold is a concentration of 30,000 parts per million of carbon dioxide.

* * * * *